United States Patent

(12) United States Patent
Saito

(10) Patent No.: US 11,330,962 B2
(45) Date of Patent: May 17, 2022

(54) ENDOSCOPE SYSTEM, PROCESSOR DEVICE, AND METHOD OF OPERATING ENDOSCOPE SYSTEM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 883 days.

(21) Appl. No.: 15/961,880

(22) Filed: Apr. 25, 2018

(65) Prior Publication Data
US 2018/0235439 A1 Aug. 23, 2018

Related U.S. Application Data

(63) Continuation of application No. PCT/JP2016/079248, filed on Oct. 3, 2016.

(30) Foreign Application Priority Data

Oct. 30, 2015 (JP) .............................. JP2015-213962

(51) Int. Cl.
*A61B 5/1455* (2006.01)
*A61B 1/00* (2006.01)
(Continued)

(52) U.S. Cl.
CPC ........ *A61B 1/00009* (2013.01); *A61B 1/0005* (2013.01); *A61B 1/041* (2013.01);
(Continued)

(58) Field of Classification Search
None
See application file for complete search history.

(56) References Cited

U.S. PATENT DOCUMENTS

2012/0188351 A1 7/2012 Kaku
2013/0018255 A1 1/2013 Kitamura et al.
(Continued)

FOREIGN PATENT DOCUMENTS

JP 2007-125245 5/2007
JP 2011-212245 10/2011
(Continued)

OTHER PUBLICATIONS

"International Search Report (Form PCT/ISA/210) of PCT/JP2016/079248", dated Dec. 27, 2016, with English translation thereof, pp. 1-2.
(Continued)

*Primary Examiner* — Marjan Fardanesh
(74) *Attorney, Agent, or Firm* — JCIPRNET

(57) ABSTRACT

An endoscope system has an oxygen saturation calculation unit that calculates the oxygen saturation of an observation object, and includes an image acquisition unit that acquires a preliminarily captured image that is an image of the observation object, a correction unit that corrects an LUT that the oxygen saturation calculation unit uses for the calculation of the oxygen saturation, using the preliminarily captured image, a determination unit that determines a success or failure of the correction, and a warning unit that performs warning in a case where a determination result obtained by the determination unit is a failure.

11 Claims, 12 Drawing Sheets

(51) Int. Cl.
*G02B 23/24* (2006.01)
*G02B 23/26* (2006.01)
*A61B 1/04* (2006.01)
*G06T 5/00* (2006.01)
*G06T 5/50* (2006.01)
*A61B 1/06* (2006.01)
*A61B 5/00* (2006.01)
*A61B 5/1459* (2006.01)

(52) U.S. Cl.
CPC ............ *A61B 1/043* (2013.01); *A61B 1/0638* (2013.01); *A61B 1/0646* (2013.01); *A61B 5/0084* (2013.01); *A61B 5/1459* (2013.01); *A61B 5/14552* (2013.01); *A61B 5/7246* (2013.01); *G02B 23/24* (2013.01); *G02B 23/26* (2013.01); *G06T 5/009* (2013.01); *G06T 5/50* (2013.01); *A61B 5/743* (2013.01); *G06T 2207/10068* (2013.01); *G06T 2207/10152* (2013.01); *G06T 2207/30104* (2013.01)

(56) References Cited

U.S. PATENT DOCUMENTS

2013/0030268 A1* 1/2013 Saito .................. A61B 1/05
600/325

2013/0235177 A1 9/2013 Saito
2014/0152790 A1 6/2014 Saito et al.
2016/0183774 A1 6/2016 Shiraishi

FOREIGN PATENT DOCUMENTS

| | | |
|---|---|---|
| JP | 2012-143464 | 8/2012 |
| JP | 2012-152266 | 8/2012 |
| JP | 2013-022341 | 2/2013 |
| JP | 2013-188244 | 9/2013 |
| JP | 2015039617 | 3/2015 |
| JP | 2015054062 | 3/2015 |
| JP | 2015-066127 | 4/2015 |
| WO | 2013035531 | 3/2013 |
| WO | 2014132742 | 9/2014 |

OTHER PUBLICATIONS

"Written Opinion (Form PCT/ISA/237)", dated Dec. 27, 2016, with English translation thereof, pp. 1-7.

"Search Report of Europe Counterpart Application", dated Nov. 16, 2018, p. 1-p. 8.

* cited by examiner

ENDOSCOPE SYSTEM, PROCESSOR DEVICE, AND METHOD OF OPERATING ENDOSCOPE SYSTEM

CROSS-REFERENCE TO RELATED APPLICATIONS

This application is a Continuation of PCT International Application No. PCT/JP2016/79248, filed on Oct. 3, 2016, which claims priority under 35 U.S.C. § 119(a) to Japanese Patent Application No. 2015-213962, filed on Oct. 30, 2015. Each of the above application(s) is hereby expressly incorporated by reference, in its entirety, into the present application.

BACKGROUND OF THE INVENTION

1. Field of the Invention

The present invention relates to an endoscope system, a processor device, and a method of operating an endoscope system that calculate the oxygen saturation of an observation object.

2. Description of the Related Art

In the medical field, it is general to perform diagnosis using endoscope systems including a light source device, an endoscope, and a processor device. Particularly, endoscope systems for obtaining an image in which specific tissues or structures, such as blood vessels or duct structures, are enhanced simply not only by naturally observing an observation object but also by devising the wavelength of illumination light or by performing signal processing, such as spectrum estimation processing, on an image obtained by imaging the observation object have become widespread.

In recent years, there have also been endoscope systems for obtaining living body functional information, using the image obtained by imaging the observation object. For example, diagnosis of a lesion using an image (hereinafter referred to as an oxygen saturation image) representing the oxygen saturation of hemoglobin included in the observation object is being performed. In order to calculate the oxygen saturation, the observation object is imaged with a plurality of illumination light beams having different wavelength ranges, respectively, as described, for example, in JP2013-022341A. The observation object is imaged using at least light beams of wavelength ranges having different light absorption coefficients for oxygenated hemoglobin and reduced hemoglobin for the illumination light beams. Then, predetermined arithmetic values are calculated using pixel values of the obtained image, and the oxygen saturation of the observation object is calculated using a look-up table showing a correlation in which the arithmetic values are correlated with the oxygen saturation. There is a case where the correlation between the arithmetic values and the oxygen saturation may vary depending on various parts such as the esophagus, the stomach, and the large intestine, individual differences between patients, such as the sex and age, or the like. For this reason, in JP2013-022341A, preliminary capturing in which a normal part of the observation object is imaged is performed to correct the look-up table before the oxygen saturation of the observation object is actually calculated.

In an endoscopic image, there is a case where the reflection of the illumination light is strong, and halation with partial white collapse is partially generated. As a result, the oxygen saturation cannot be accurately calculated regarding the halation portion. In consideration of this, an endoscope system that detects the halation of the oxygen saturation image is known (WO2013-035531A). Additionally, in a case where the movement of the observation object is large, there is a case where the accuracy of the oxygen saturation may decrease. For this reason, an endoscope system that displays a warning sign showing the possibility that the reliability of the oxygen saturation may decrease in a case where the movement of the observation object is large is known (JP2013-188244A).

In addition, in a case where residual substances, residual liquid, or the like has adhered to the observation object, in a case where the relative distance (hereinafter referred to as an observation distance) between the endoscope and the observation object is extremely short or long, or in a case where an artificial object, such as a treatment tool, is inserted into a subject, the oxygen saturation may be accurately calculated. With respect to these, although these are not endoscope systems that calculate the oxygen saturation, a fluorescent endoscope system (JP2007-125245A) that detects the residual substances adhering to the observation object, a laparoscope system (JP2011-212245A) that detects the distance between the treatment tool and the observation object and performs warning in a case where the treatment tool has approached the observation object, and an endoscope system (JP2012-152266A) adapted not to perform unnecessary image processing on the artificial object, such as a treatment tool, are known.

SUMMARY OF THE INVENTION

In a case where the look-up table in which the arithmetic values are correlated with the oxygen saturation is corrected by performing the preliminary capturing as in JP2013-022341A, in the preliminary capturing, it is necessary to appropriately image the normal portion of the observation object. For example, since the look-up table cannot be accurately corrected in a case where halation is present on a preliminarily captured image obtained by the preliminary capturing, the preliminarily captured image is required to have no halation. Similarly, it is required that there is no blur resulting from the relative movement between the observation object and the endoscope, the observation distance is not excessively short or excessively long, there are no adhering substances, such as residual substances, on the observation object, and there is no reflection of the artificial object or the like. Instead of correcting the look-up table, the same applies to a case where the calculated oxygen saturation is compensated for.

However, since the preliminary capturing is also performed by imaging the observation object with the endoscope, there is a case where the reflection of the halation, the movement and the observation distance, the adhering substances, the artificial object or the like may also be present on the preliminarily captured image. For this reason, it is desirable that a success or failure of the correction of the look-up table correction or the compensation of the calculated oxygen saturation is determined, and in case of a failure, a doctor or the like is notified of the fact.

An object of the invention is to provide an endoscope system, a processor device, and a method of operating an endoscope system that reliably perform correction of data used for calculation of oxygen saturation or compensation of the calculated oxygen saturation by performing warning in a case where the correction of the data used for the calculation of the oxygen saturation or the compensation of the calculated oxygen saturation is a failure.

An endoscope system of the invention is an endoscope system having an oxygen saturation calculation unit that calculates oxygen saturation of an observation object, and comprises an image acquisition unit that acquires an image of the observation object, a correction unit that corrects data that the oxygen saturation calculation unit uses for the calculation of the oxygen saturation, using the image, a determination unit that determines a success or failure of the correction, and a warning unit that performs warning in a case where a determination result obtained by the determination unit is a failure.

It is preferable that the image acquisition unit acquires a plurality of the images obtained by imaging the observation object with a plurality of illumination light beams having different wavelength ranges, respectively, and the determination unit determines a success or failure of the correction for each of the images.

It is preferable that the determination unit determines a success or failure of the correction depending on a brightness of the image.

It is preferable that the determination unit determines a success or failure of the correction depending on a distribution of pixel values of the image.

It is preferable that the determination unit detects an excessively bright portion or an excessively dark portion from the image, determines the correction to be a failure in a case where the excessively bright portion or the excessively dark portion is present, and determines the correction to be a success in a case where there is no excessively bright portion or excessively dark portion.

It is preferable that the image acquisition unit acquires a plurality of the images obtained by imaging the observation object with a plurality of illumination light beams having different wavelength ranges, respectively, and the determination unit determines a success or failure of the correction, using a ratio of the plurality of the images.

It is preferable that the determination unit detects an adhering substance adhering to the observation object, determines the correction to be a failure in a case where there is an adhering substance, and determines the correction to be a success in a case where there is no adhering substance.

It is preferable that the determination unit determines a success or failure of the correction, depending on information on properties of the observation object represented by the ratio of the plurality of images.

It is preferable that the determination unit determines a success or failure of the correction depending on an amount of blood.

It is preferable that the determination unit detects reflection of an artificial object, determines the correction to be a success in a case where there is no reflection of the artificial object, and determines the correction to be a failure in a case where there is the reflection of the artificial object.

It is preferable that the determination unit determines a success or failure of the correction depending on a light emission amount of illumination light in a case where the image is captured.

It is preferable that the determination unit calculates an observation distance, using the light emission amount, and determines a success or failure of the correction depending on the observation distance.

It is preferable that the determination unit determines the correction to be a failure in a case where the observation distance is shorter than a specific distance.

It is preferable that the determination unit detects a relative movement between the observation object and an endoscope that images the observation object, using the image, and determines a success or failure of the correction depending on a magnitude of the detected movement.

It is preferable that the determination unit detects the movement, using a plurality of images obtained by imaging the observation object with the same illumination light, in the image.

It is preferable that the warning unit displays a message on a display unit.

Another endoscope system of the invention is another endoscope system having an oxygen saturation calculation unit that calculates an oxygen saturation of an observation object, and comprises an image acquisition unit that acquires an image of the observation object; a compensation amount calculation unit that calculates an amount of compensation for the oxygen saturation that the oxygen saturation calculation unit calculates using the image; a compensation unit that compensates for the oxygen saturation calculated by the oxygen saturation calculation unit in accordance with the amount of compensation; a determination unit that determines a success or failure of the compensation; and a warning unit that performs warning in a case where a determination result obtained by the determination unit is a failure.

A processor device of the invention is a processor device having an oxygen saturation calculation unit that calculates an oxygen saturation of an observation object, and comprises an image acquisition unit that acquires an image of the observation object, a correction unit that corrects data that the oxygen saturation calculation unit uses for the calculation of the oxygen saturation, using the image, a determination unit that determines a success or failure of the correction, and a warning unit that performs warning in a case where a determination result obtained by the determination unit is a failure.

A method of operating an endoscope system of the invention is a method of operating an endoscope system having an oxygen saturation calculation unit that calculates an oxygen saturation of an observation object. The method comprises a step of acquiring an image of the observation object with an image acquisition unit; a step of correcting data that the oxygen saturation calculation unit uses for the calculation of the oxygen saturation, using the image, with the correction unit; a step of determining a success or failure of the correction with a determination unit; and a step of performing warning through a warning unit in a case where a determination result obtained by the determination unit is a failure.

The endoscope system, the processor device, and the method of operating an endoscope system of the invention can reliably perform the correction of the data used for the calculation of the oxygen saturation or the compensation of the calculated oxygen saturation because the warning is performed in a case where the correction of the data used for the calculation of the oxygen saturation or the compensation of the calculated oxygen saturation is a failure.

DESCRIPTION OF THE PREFERRED EMBODIMENTS

First Embodiment

Figure 1:
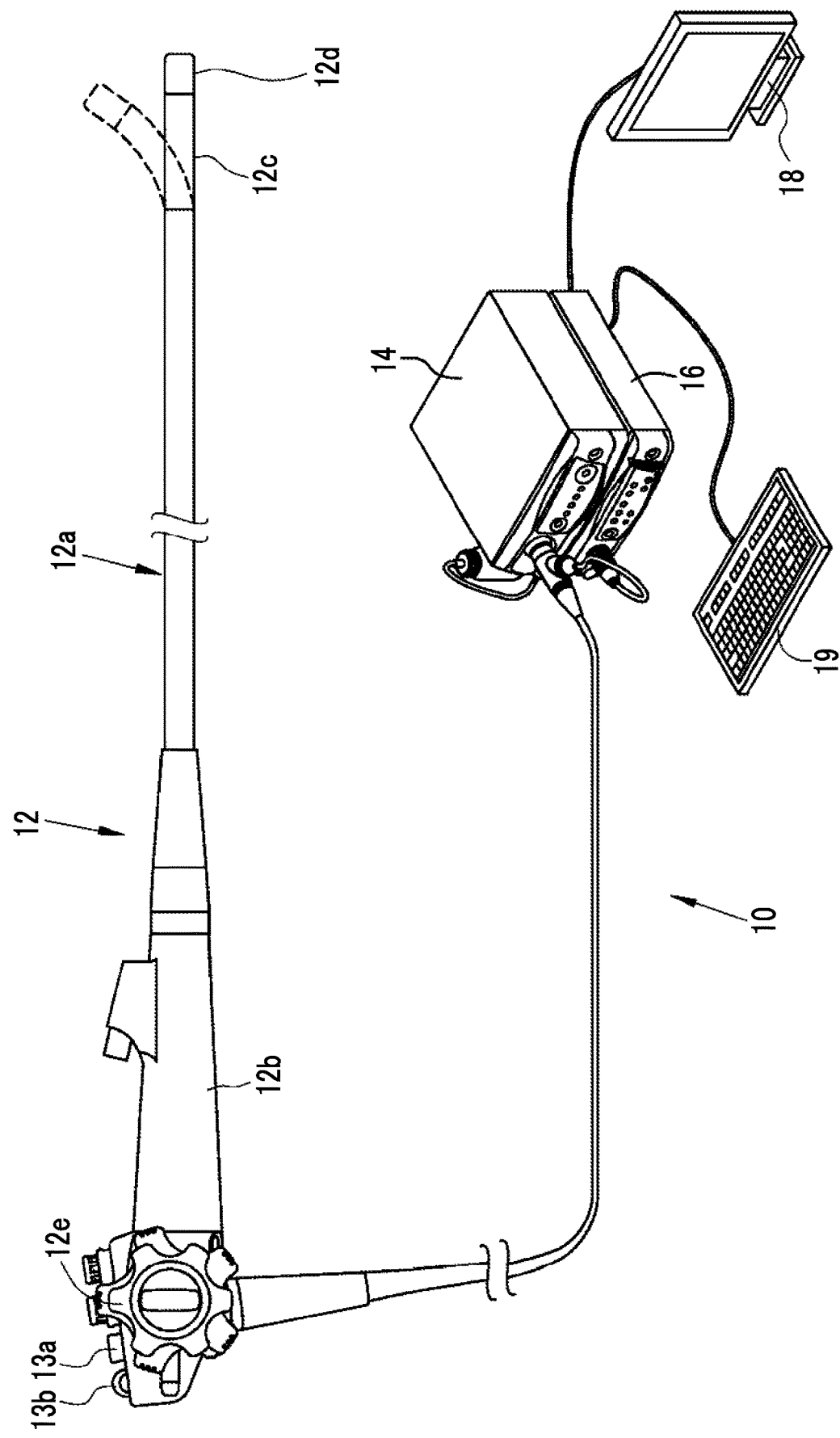
FIG. 1 is an external view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14 and is electrically connected to the processor device 16. The endoscope 12 has an insertion part 12a to be inserted into a subject, an operating part 12b provided at a base end portion of the insertion part 12a, and a bending part 12c and a distal end part 12d provided on a distal end side of the insertion part 12a. By operating an angle knob 12e of the operating part 12b, the bending part 12c makes a bending motion. The distal end part 12d is directed in a desired direction by this bending motion.

Additionally, the operating part 12b is provided with a mode changeover switch 13a and a zooming operation part 13b other than the angle knob 12e. The mode changeover switch 13a is used for switching operation in an observation mode. The endoscope system 10 has two observation modes of a normal observation mode and an oxygen saturation observation mode. The normal observation mode is an observation mode in which white light is radiated to image an observation object, and a natural-tone image (hereinafter referred to as a normal image) is displayed on the monitor 18. The oxygen saturation observation mode is an observation mode in which the oxygen saturation of the observation object is calculated using an image obtained by imaging the observation object, using G light beams of wavelength ranges having different light absorption coefficients for oxygenated hemoglobin and reduced hemoglobin, and an oxygen saturation image is displayed on the monitor 18.

The processor device 16 is electrically connected to the monitor 18 and the console 19. The monitor 18 outputs and displays the images in the respective observation modes, image information accompanying the images, and the like. The console 19 functions as a user interface that receives an input operation, such as function setting. In addition, an external recording unit (not illustrated) that records the images, the image information, and the like may be connected to the processor device 16.

Figure 2:
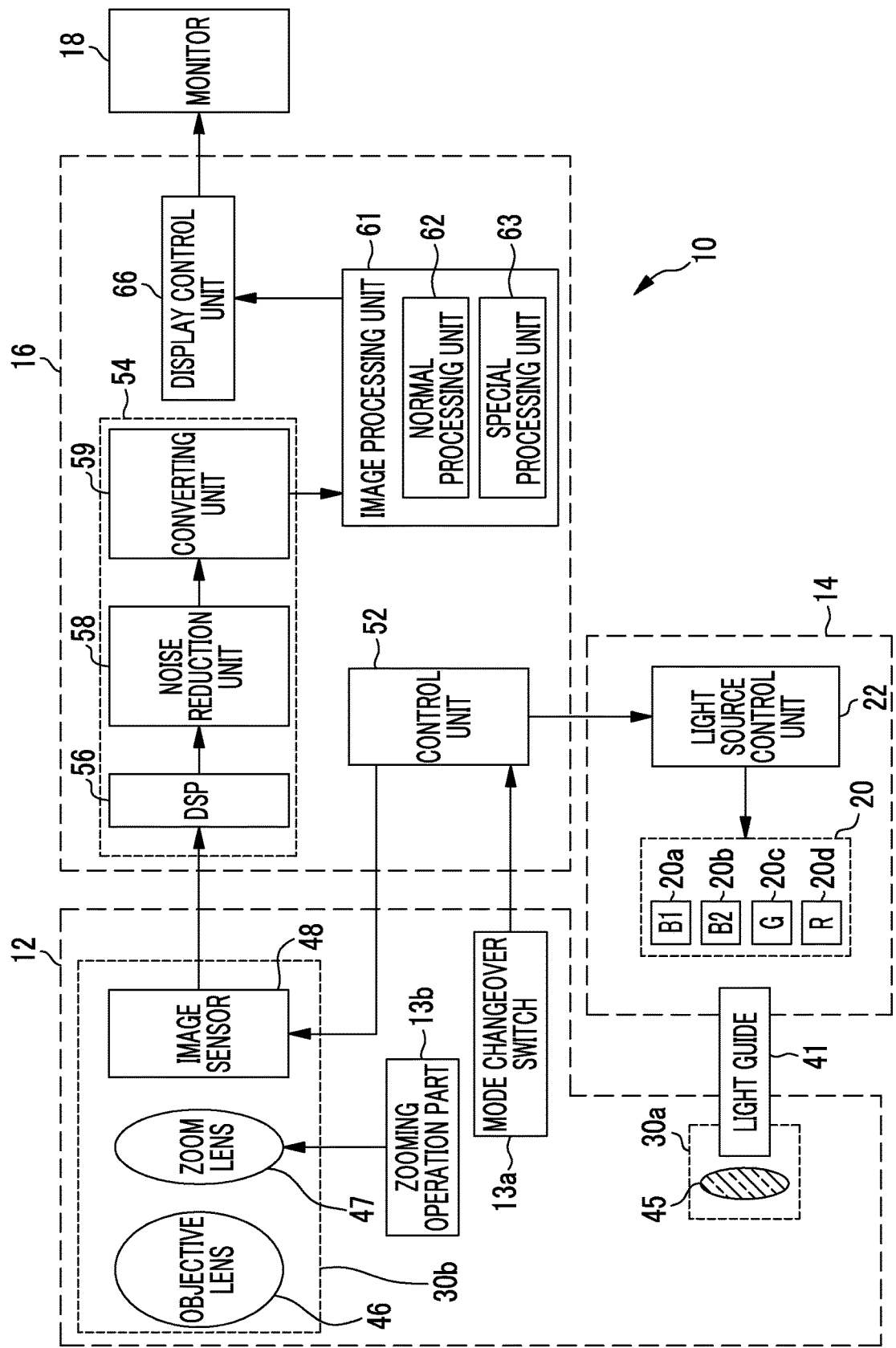
FIG. 2 is a block diagram of an endoscope system.

As illustrated in FIG. 2, the light source device 14 includes a light source unit 20 that emits illumination light, and a light source control unit 22 that controls driving of the light source unit 20.

The light source unit 20 includes four light sources of a B1 light source 20a, a B2 light source 20b, a G light source 20c, and an R light source 20d. In the present embodiment, the B1 light source 20a, the B2 light source 20b, the G light source 20c, and the R light source 20d are all light emitting diodes (LEDs). Instead of such LEDs, a combination of a laser diode (LD), a fluorescent body, and a band limiting filter, a combination of a lamp, such as a xenon lamp, and a band limiting filter, or the like can be used for the light source unit 20.

Both the B1 light source 20a and the B2 light source 20b are blue light sources that emit blue light. However, central wavelengths and wavelength ranges are different between blue light (hereinafter referred to as B1 light) emitted from the B1 light source 20a, and blue light (hereinafter referred to as B2 light) emitted from the B2 light source 20b. The B1 light is a narrowband blue light of which the central wavelength and the wavelength range are 470±10 nm. The central wavelength and the wavelength range of the B1 light are a central wavelength and a wavelength range, at which a difference in light absorption coefficient between oxygenated hemoglobin and reduced hemoglobin becomes approximately maximum, in a blue wavelength range. Hence, the B1 light is used in the oxygen saturation observation mode. Meanwhile, the B2 light is a broadband blue light of which the central wavelength is about 450±10 nm and the wavelength range is about 400 nm to 500 nm. The B2 light is used in the normal observation mode and the oxygen saturation observation mode.

The G light source 20c is a green light source that emits broadband green light (hereinafter referred to as G light) of which the central wavelength is 540±20 nm and the wavelength range is about 480 nm to 600 nm. The R light source 20d is a red light source that emits broadband red light (hereinafter referred to as R light) of which the central wavelength is 640±20 nm and the wavelength range is about 600 nm to 700 nm. The G light and the R light are used in the normal observation mode and the oxygen saturation observation mode.

The light source control unit 22 controls the optical spectrum and the light quantity of the illumination light by controlling the timing of turning on/off the respective light sources 20a to 20d that constitute the light source unit 20, the light emission amount thereof, and the like. In the case of the normal observation mode, the light source control unit 22 turns on the B2 light source 20b, the G light source 20c, and the R light source 20d. For this reason, in the normal observation mode, the white light consisting of the B2 light, the G light, and the R light becomes the illumination light.

In the oxygen saturation observation mode, the light source control unit 22 switches the illumination light for each imaging frame. Specifically, the B1 light source 20a is turned on in a certain imaging frame (hereinafter referred to as a first frame), and the B2 light source 20b, the G light source 20c, and the R light source 20d are turned on in the next imaging frame (hereinafter referred to as a second frame). That is, the illumination light in the first frame is the B1 light, and the illumination light in the second frame is the white light consisting of the B2 light, the G light, and the R light. Additionally, in a case where the normal observation mode is shifted to the oxygen saturation observation mode, the light source control unit 22 sequentially turns on the B1 light source 20a, the B2 light source 20b, the G light source 20c, and the R light source 20d in accordance with the imaging frames at least once, and sequentially switches the illumination light to the B1 light, the B2 light, the G light, and the R light. This is for correcting a look-up table (LUT) 75 (refer to FIGS. 3 and 4) used for the calculation of the oxygen saturation.

The above various kinds of illumination light emitted from the light source unit 20 enter a light guide 41. The light guide 41 is built in the endoscope 12 and a universal cord (a cord that connects the endoscope 12, and the light source device 14 and the processor device 16 to each other), and propagates the illumination light to the distal end part 12d of the endoscope 12. In addition, multimode fiber can be used as the light guide 41. As an example, a fine-diameter fiber cable of which the core diameter is 105 µm, the clad diameter is 125 µm, and a diameter including a protective layer used as an outer cover is φ0.3 mm to 0.5 mm can be used.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object with reflected light, scattered light, or the like (including fluorescence emitted from the observation object, fluorescence due to medicine administered to the observation object) of the illumination light returning from the observation object via the objective lens 46 and the zoom lens 47. In addition, the zoom lens 47 is moved by the operation of the zooming operation part 13b, and magnifies or reduces the observation object to be imaged by the image sensor 48.

The image sensor 48 is a color sensor of a primary color system, and three kinds of pixels, a blue pixel (B pixel) provided with a blue (B) color filter, a green pixel (G pixel) provided with a green (G) color filter, and a red pixel (R pixel) provided with a red (R) color filter. For this reason, in a case where the observation object is imaged by the image sensor 48, three kinds of images of a blue image (B image), a green image (G image), and a red image (R image), are obtained.

In addition, a color sensor of a complementary color system can also be used for the image sensor 48. The color sensor of the complementary color system has, for example, a cyan pixel provided with a cyan color filter, a magenta pixel provided with a magenta color filter, a yellow pixel provided with a yellow color filter, and a green pixel provided with a green color filter. Images in the respective colors obtained in a case where the color sensor of the complementary color system is used can be converted into the B image, the G image, and the R image that are the same as those in the above embodiment.

In the case of the oxygen saturation observation mode, the illumination light in the first frame is the B1 light and does not include the green light and red light, and only the B image is substantially obtained in the first frame of the oxygen saturation observation mode. Meanwhile, since the illumination light in the second frame of the oxygen saturation observation mode is the white light, the B image, the G image, and the R image are obtained. In the following, for distinction, the B image obtained in the first frame is referred to as a B1 image, and the B image obtained in the second frame is referred to as a B2 image.

In the oxygen saturation observation mode, there is "preliminary capturing" in which images used for the correction of the LUT 75 used for calculation of oxygen saturation are obtained other than the above-described "main capturing" in which the oxygen saturation of the observation object is actually calculated and the images to be used for the generation of the oxygen saturation image are obtained. Since the preliminary capturing is imaging for the correction, a normal portion of the observation object is imaged. The normal portion of the observation object is a portion that is considered that there are no clear lesions, adhering substances, or the like and an abnormality does not occur in the oxygen saturation. In the following, the B1 image, the B2 image, the G image, and the R image obtained by performing the main capturing of "the portion for actually calculating the oxygen saturation" are referred to as a mainly captured image 91 (refer to FIG. 3), and the B1 image, the B2 image, the G image, and the R image obtained by performing preliminary capturing of "the normal portion of the observation object for correction" are referred to as a preliminarily captured image 92 (refer to FIG. 3). In the present embodiment, in a case where the normal observation mode is shifted to the oxygen saturation observation mode, the preliminary capturing is performed prior to the main capturing. However, the preliminary capturing can also be performed after the main capturing.

The processor device 16 includes a control unit 52, an image acquisition unit 54, an image processing unit 61, and a display control unit 66. The control unit 52 receives input of a mode switching signal from the mode changeover switch 13a, controls the light source control unit 22 and the image sensor 48, and switches between the observation modes. Specifically, the control unit 52 performs designation of the type and the light quantity of the illumination light for the light source control unit 22, control of the length of the exposure time of the image sensor 48 and the gain at the time of image output therefrom, synchronous control of the switching timing of the imaging frames and the illumination light, and the like. For example, the processor device 16 has a central processing unit (CPU), and the CPU functions as the control unit 52, the image acquisition unit 54, the image processing unit 61, and the display control unit 66.

The image acquisition unit 54 acquires images of the observation object in respective colors from the image sensor 48. In the case of the normal observation mode, the B image, the G image, and the R image are acquired from the image sensor 48. Additionally, in the case of the oxygen saturation observation mode, the B1 image is acquired in the first frame, and the B2 image, the G image, and the R image are acquired in the second frame. That is, the image acquisition unit 54 acquires a plurality of images obtained by imaging the observation object with a plurality of kinds of illumination light having different wavelength ranges, respectively. Additionally, the image acquisition unit 54 has a digital signal processor (DSP) 56, a noise reduction unit 58, and a converting unit 59, and performs various kinds of processing on an image acquired by these units.

The DSP 56 performs various kinds of processing, such as defect correction processing, offset processing, gain correction processing, linear matrix processing, gamma conversion processing, demosaicing processing, and YC conversion processing, on the acquired image.

The defect correction processing is the processing of correcting the pixel value of a pixel corresponding to a defective pixel of the image sensor 48. The offset processing is the processing of removing a dark current component from the image subjected to the defect correction processing, and setting an accurate zero level. The gain correction processing is the processing of adjusting a signal level by multiplying the image subjected to the offset processing by a gain. The linear matrix processing is the processing of enhancing color reproducibility on the image subjected to the offset processing. The gamma conversion processing is the processing of adjusting the brightness or saturation of the image after the linear matrix processing. The demosaicing processing (also referred to as equalization processing or synchronization processing) is the processing of interpolating the pixel value of a missing pixel, and is performed on the image after the gamma conversion processing. The missing pixel is a pixel with no pixel value because pixels in other colors are disposed in the image sensor 48. For example, since the B image is an image obtained by imaging the observation object with the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image. The YC conversion processing is the processing of converting the image after the demosaicing processing into a luminance image Y, a color difference image Cb, and a color difference image Cr.

The noise reduction unit 58 performs noise reduction processing using, for example, a moving average method, a median filter method, or the like on the luminance image Y, the color difference image Cb, and the color difference image Cr. The converting unit 59 re-converts the luminance image Y, color difference image Cb, and the color difference image Cr after the noise reduction processing into images in respective colors of BGR.

The image processing unit 61 has a normal processing unit 62 and a special processing unit 63. The normal processing unit 62 operates in the normal observation mode, and performs color conversion processing, color enhancement processing, and structure enhancement processing on the images in the respective colors of BGR to generate a normal image. In the color conversion processing, 3×3 matrix processing, gradation transformation processing, three-dimensional look-up table (LUT) processing, and the like are performed on the images in the respective colors of BGR. The color enhancement processing is the processing of enhancing the colors of an image, and the structure enhancement processing is the processing of enhancing, for example, the structure of an observation object, such as a blood vessel or a pit pattern. The display control unit 66 converts the normal image acquired from the normal processing unit 62 into a format suitable for display, and inputs the converted image to the monitor 18. Accordingly, the monitor 18 displays the normal image.

Figure 3:
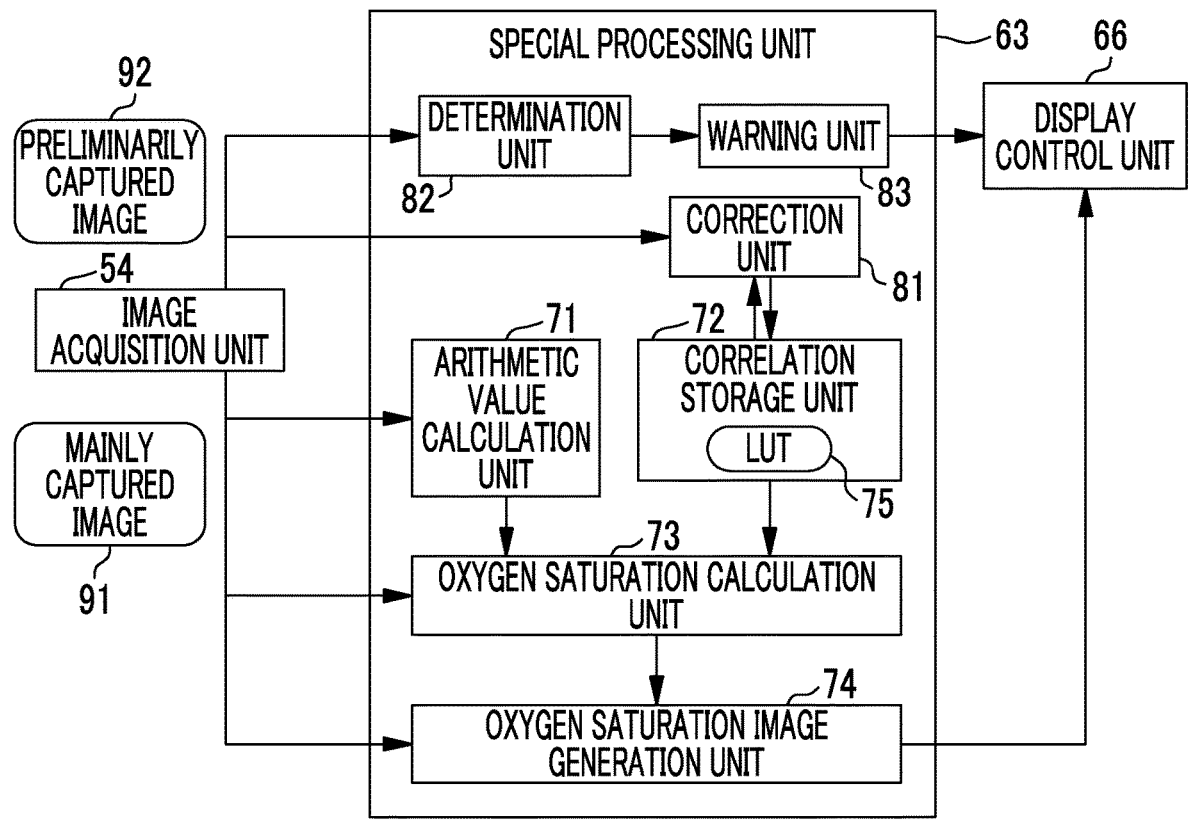
FIG. 3 is a block diagram of a special processing unit.

The special processing unit 63 operates in the oxygen saturation observation mode, calculates the oxygen saturation of the observation object, using the mainly captured image, and generates the oxygen saturation image. As illustrated in FIG. 3, the special processing unit 63 includes an arithmetic value calculation unit 71, a correlation storage unit 72, an oxygen saturation calculation unit 73, and an oxygen saturation image generation unit 74.

The arithmetic value calculation unit 71 acquires a mainly captured image 91 from the image acquisition unit 54, performs computation, using the pixel values of the mainly captured image 91, and calculates arithmetic values to be used for the calculation of the oxygen saturation. Specifically—the arithmetic value calculation unit 71 calculates a ratio B1/G of the B1 image to the G image and a ratio R/G of the R image to the G image, respectively, for each pixel. The ratio B1/G and the ratio R/G are arithmetic values calculated by the arithmetic value calculation unit 71, and are computation results of computation using the pixel values of the image acquired by the image acquisition unit 54. The ratio B1/G are mainly dependent on the oxygen saturation and the amount of blood, and the ratio R/G is mainly dependent on the amount of blood. For this reason, in a case where the balance between the ratio B1/G and the ratio R/G is taken into consideration, it is possible to obtain the oxygen saturation of the observation object excluding dependence on the amount of blood.

Figure 4:
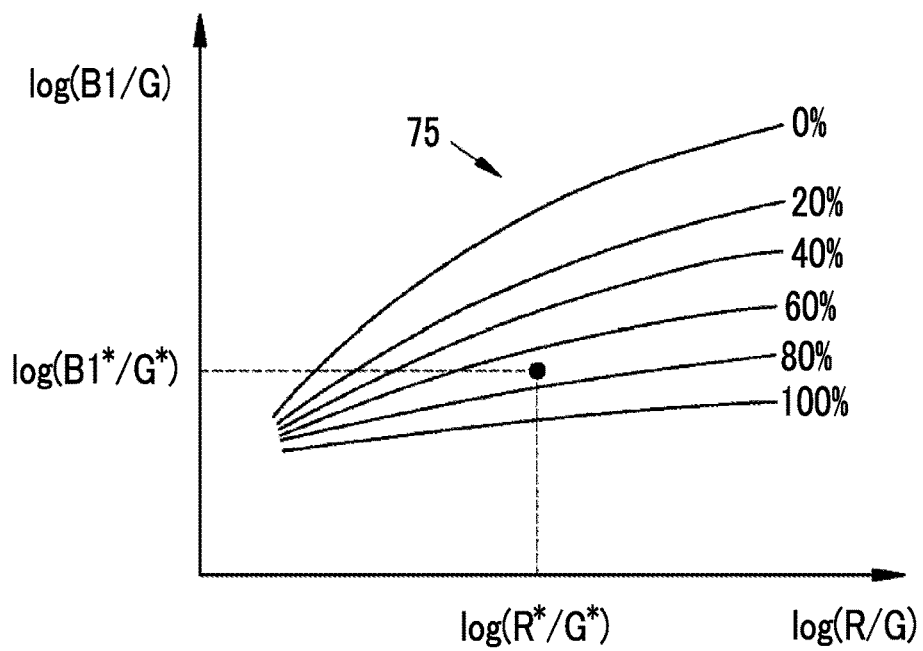
FIG. 4 is a graph illustrating the contents of an LUT used for calculation of oxygen saturation.

The correlation storage unit 72 stores a correlation, in which the ratio B1/G that is a computation result of the arithmetic value calculation unit 71 is correlated with the ratio R/G with the oxygen saturation, in a look-up table (LUT) 75. The LUT 75 is data that the oxygen saturation calculation unit 73 uses for the calculation of the oxygen saturation. As illustrated in FIG. 4, the correlation stored in the LUT 75 is a two-dimensional table in which isoplethic lines of the oxygen saturation are defined in a two-dimensional space having the ratio B1/G and the ratio R/G as axes. In addition, the positions and the shapes of the isoplethic lines for the ratio B1/G and the ratio R/G are obtained in advance by physical simulation of light scattering. In addition, the correlation storage unit 72 stores the correlation between the ratio B1/G and the ratio R/G and the oxygen saturation in log scales.

The oxygen saturation calculation unit 73 refers to the LUT 75 stored in the correlation storage unit 72, and calculates the oxygen saturation corresponding to the ratio B1/G and the ratio R/G calculated by the arithmetic value calculation unit 71. For example, in a case where, in a specific pixel, the value of the ratio B1/G is B1*/G* and the value of R/G is R*/G*, the oxygen saturation corresponding to these values is "70%" referring to the LUT 75 (refer to FIG. 4). For this reason, the oxygen saturation calculation unit 73 calculates the oxygen saturation of this specific pixel as "70%".

In addition, the ratio B1/G and the ratio R/G hardly become extremely large values, or conversely, hardly become extremely small values. That is, a combination of the ratio B1/G and the ratio of R/G hardly becomes a combination that exceeds an upper-limit isoplethic line representing an oxygen saturation of "100%", or a combination that falls below a lower-limit isoplethic line representing an oxygen saturation of "0%". The oxygen saturation calculation unit 73 sets the oxygen saturation to 100% in a case where the oxygen saturation exceeds 100%, and sets the oxygen saturation as 0% in a case where the oxygen saturation falls below 0%.

The oxygen saturation image generation unit 74 generates the oxygen saturation image, using the mainly captured image 91 and the oxygen saturation calculated by the oxygen saturation calculation unit 73. Specifically, the oxygen saturation image generation unit 74 generates an image (hereinafter a base image), which becomes a base of the oxygen saturation image using the B2 image, the G image, and the R image that are obtained in the second frame, in the mainly captured image 91. The base image is generated by performing the color conversion processing, the color enhancement processing, and the structure enhancement processing on the B2 image, the G image, and the R image. That is, the base image is a normal image generated using the images obtained in the second frame in the oxygen saturation observation mode. In a case where the base image is generated, the oxygen saturation image generation unit 74 applies colors to the base image, using the oxygen saturation calculated by the oxygen saturation calculation unit 73, and generates an oxygen saturation image 77 (refer to FIG. 5) representing the oxygen saturation depending on colors.

Figure 5:
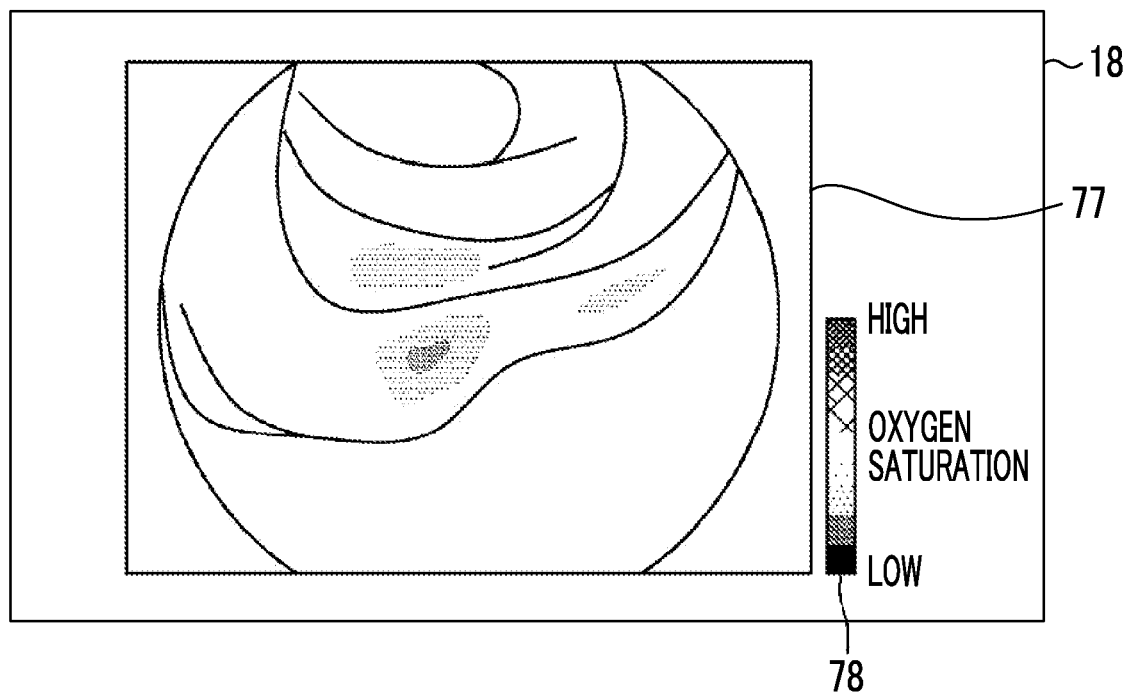
FIG. 5 is an oxygen saturation image.

In the case of the oxygen saturation observation mode, the display control unit 66 acquires the oxygen saturation image 77 from the oxygen saturation image generation unit 74. By converting the acquired oxygen saturation image 77 into a format suitable for display to input the converted image to the monitor 18, the display control unit 66 displays the oxygen saturation image 77 on the monitor 18, as illustrated in FIG. 5. Additionally, in a case where the oxygen saturation image 77 is displayed on the monitor 18, the display control unit 66 displays color scales 78 showing a correspondence relationship between the colored color and high or low height oxygen saturation on the monitor 18.

As described above, the special processing unit 63 calculates the oxygen saturation, using the mainly captured image 91, in the oxygen saturation observation mode, and the special processing unit 63 corrects the LUT 75 used for the calculation of the oxygen saturation in a case where the oxygen saturation image 77 is generated. For this reason, the special processing unit 63 includes a correction unit 81 other than the above respective units.

The correction unit 81 acquires the preliminarily captured image 92 from the image acquisition unit 54, and corrects the LUT 75, using this preliminarily captured image 92. Specifically, the correction unit 81 calculates the ratio B1/G and the ratio R/G for each pixel, using the B1 image, the G image, and the R image of the preliminarily captured image 92, and corrects the LUT 75, using a representative value of the calculated ratio B1/G and a representative value of the calculated ratio R/G. In the present embodiment, the representative values of the ratio B1/G and the ratio R/G are average values. However, statistic amounts, such as median values or most frequent values, can be representative values.

Figure 6:
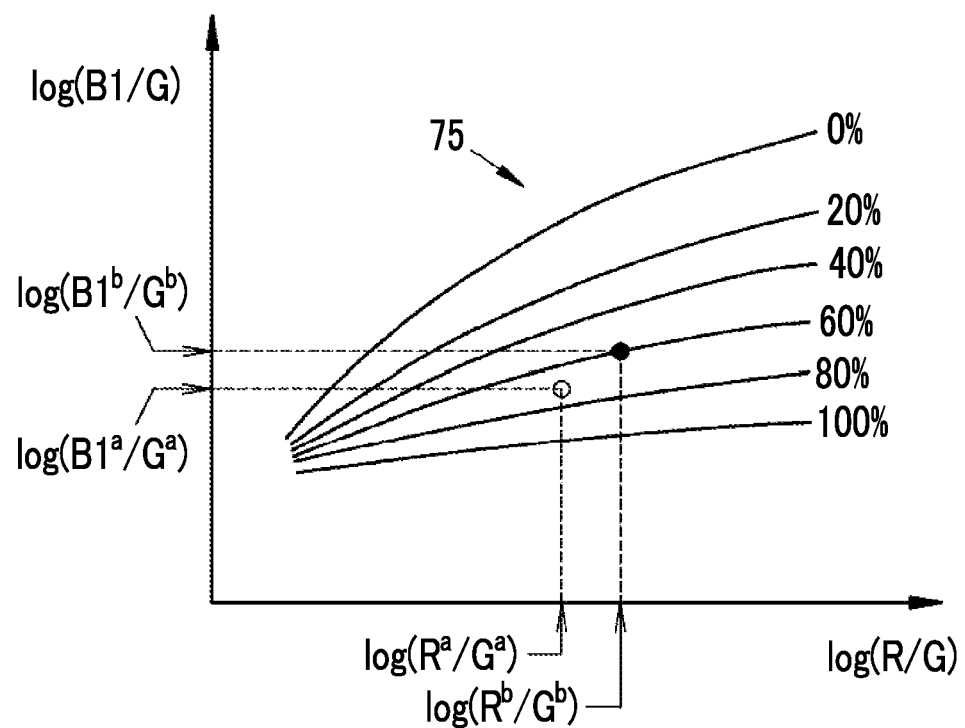
FIG. 6 is a graph illustrating a deviation between an ideal observation object and an actual observation object.

Since the normal portion of the observation object is imaged in the preliminary capturing, in the case of an ideal observation object assumed in the simulation for calculating the LUT 75, the "representative value of the ratio B1/G", the "representative value" of the ratio R/G, and the "value of the oxygen saturation correlated with the representative values of these ratios by the LUT 75" become specific values. For example, as illustrated in FIG. 6, the representative value of the ratio B1/G calculated using an image obtained by imaging the normal portion of the ideal observation object becomes $B1^a/G^a$, the representative value of the ratio R/G becomes $R^a/G^a$, and the oxygen saturation becomes 70%. Meanwhile, since there is an individual difference or the like in an actual observation object, there is a case where deviation may occur in the "representative value of the ratio B1/G" and the "representative value" of the ratio R/G calculated using the preliminarily captured image 92 obtained by imaging the actual observation object, for example, the representative value of the ratio B1/G may become $B1^b/G^b$ and the representative value of the ratio R/G may become $R^b/G^b$. In this case, in a case where the oxygen saturation is calculated using the LUT 75, the value of the oxygen saturation is 60%.

Figure 7:
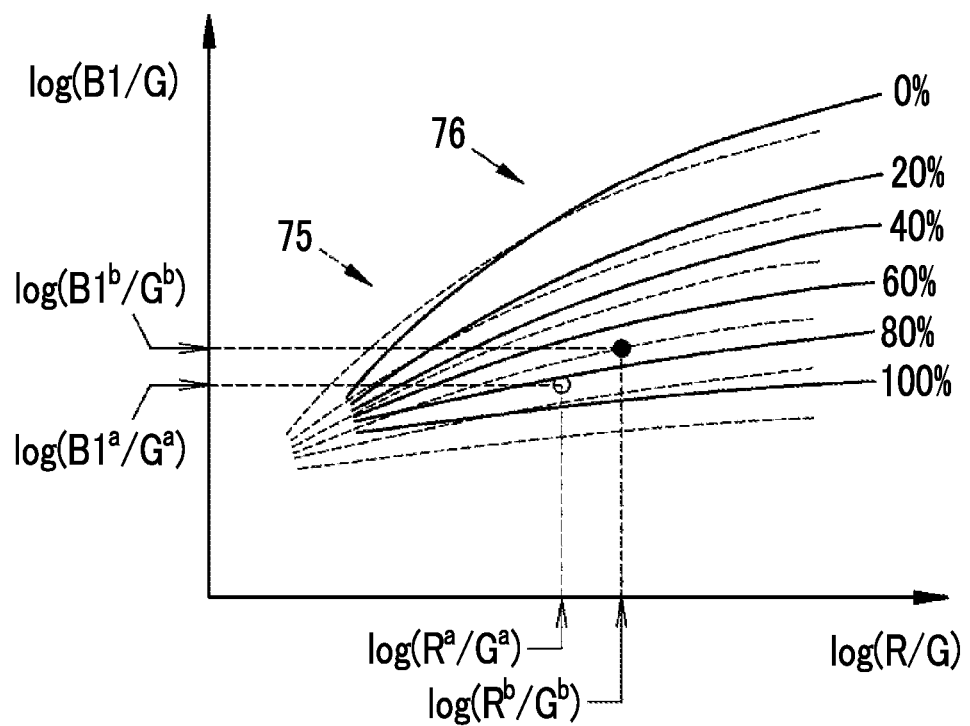
FIG. 7 is a graph illustrating a method of correcting the LUT used for the calculation of the oxygen saturation.

However, the "value of the oxygen saturation" is not easily affected by the individual difference or the like of the observation object, and is substantially constant (for example, 70%) in any observation object in a case where the normal portion is observed. For this reason, as illustrated in FIG. 7, the correction unit 81 moves the isoplethic lines represented by the LUT 75, and corrects the contents of the LUT 75 so as to obtain the value (70%) in the case where the normal portion is observed from the ratio $B1^b/G^b$ and the ratio $R^b/G^b$ calculated using the preliminarily captured image 92. This is the correction performed by the correction unit 81.

In addition, a relative positional relationship of the isoplethic lines of the LUT 75 before correction to the ratio $B1^a/G^a$ and the ratio $R^a/G^a$, and a relative positional relationship of the isoplethic lines to the LUT 76 after correction to the ratio $B1^b/G^b$ and the ratio $R^b/G^b$ are equal to each other. Additionally, in a case where the correction unit 81 corrects the LUT 75, the oxygen saturation calculation unit 73 calculates the oxygen saturation, using the LUT 76 after correction. For this reason, in the oxygen saturation calculated by the oxygen saturation calculation unit 73, the influence of the individual difference or the like of the observation object is reduced.

Figure 8:
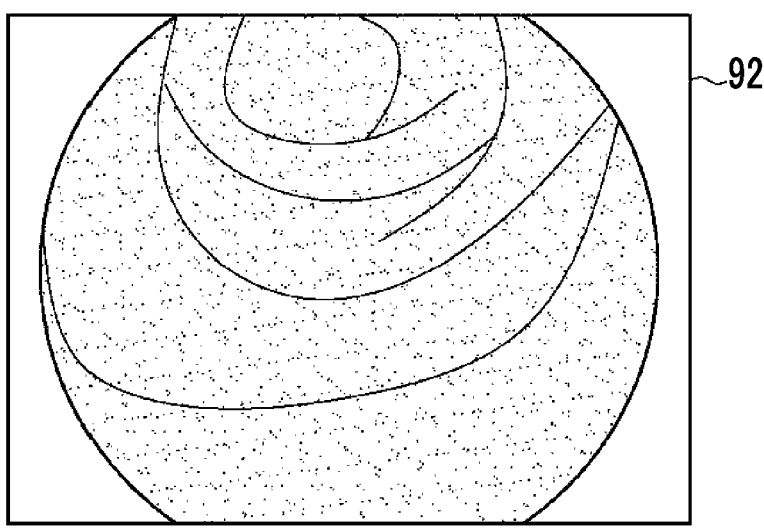
FIG. 8 is an excessively dark preliminarily captured image.
Figure 9:
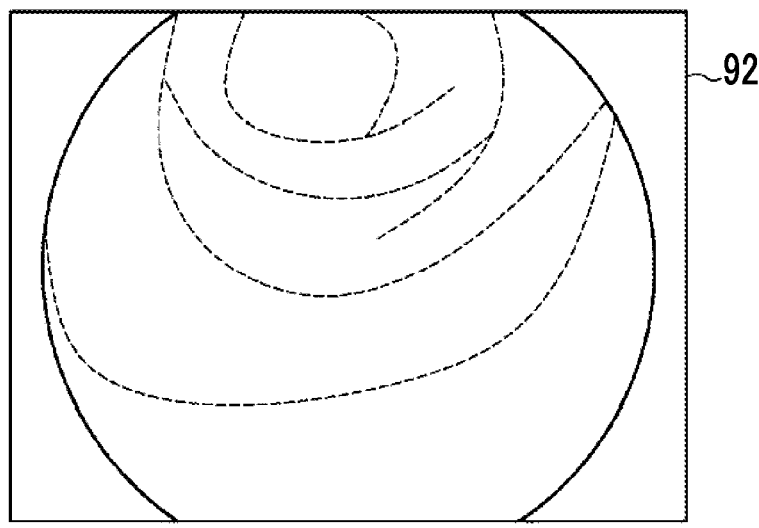
FIG. 9 is an excessively bright preliminarily captured image.

The correction unit 81 can accurately correct the LUT 75, for example, in the case of an image obtained by appropriately imaging the normal portion of the observation object by the preliminarily captured image 92. However, as illustrated in FIG. 8, even in a case where the normal portion of the observation object is imaged, the preliminarily captured image 92 may be excessively dark, for example in a case where an observation distance is unsuitable. On the contrary, as illustrated in FIG. 9, the preliminarily captured image 92 may be excessively bright. In this way, in a case where the brightness of the preliminarily captured image 92 is not suitable, the correction of the LUT 75 performed by the correction unit 81 becomes inaccurate. The "excessively bright" means being brighter than a predetermined brightness and the "excessively dark" means being darker than the predetermined brightness.

For this reason, the special processing unit 63 further includes a determination unit 82 that determines a success or failure of the correction performed by the correction unit 81 other than the above correction unit 81, and a warning unit 83 that performs warning in a case where a determination result of the determination unit 82 is a failure.

The determination unit 82 acquires the preliminarily captured image 92 used by the correction unit 81 from the image acquisition unit 54, and determines a success or failure of the correction performed by the correction unit 81 depending on the brightness of the preliminarily captured image 92. Additionally, since the image acquisition unit 54 acquires a plurality of images as the preliminarily captured image 92, the determination unit 82 determines a success or failure of the correction performed by the correction unit 81 for each of these images. That is, the determination unit 82 performs determination on the B1 image, the G image, and the R image, respectively, in the acquired preliminarily captured image 92, determines the correction performed by the correction unit 81 to be a "success" in a case where all of these determination results are "successes", and determines the correction performed by the correction unit 81 to be a "failure" in a case where any of these determination results is a "failure".

The determination unit 82 calculates the representative values (for example, the average values, the median values, the most frequent values, or the like of the pixel values)

regarding the B1 image, the G image, and the R image, respectively, compares the representative values with a lower limit threshold value (minimum value) Th1 and an upper limit threshold value (maximum value) Th2 that are set in advance, and determines the images in the respective colors. For example, in a case where the representative value of the B1 image is equal to or greater than the lower limit threshold value Th1 and equal to or smaller than the upper limit threshold value Th2, determination in the B1 image is considered to be a "success", and in the other cases, determination in the B1 image is considered to be a "failure". The same applies to the G image and the R image. For example, the lower limit threshold value Th1 is set to 5% of the maximum value (1023 in the case of 10 bits), and the upper limit threshold value Th2 is set to 80% of the maximum value.

In addition, the determination unit 82 calculates representative values regarding predetermined regions among the images in the respective colors in a case where the representative values of the images in the respective colors are calculated. The predetermined regions are, for example, central regions of images, regions excluding center portions of images, entire images, or other designated regions. The representative values can also be calculated by removing upper and lower predetermined percentages (for example, 10%) in the frequency distribution of the pixel values, thereby excluding extremely dark portions and extremely bright portions in the images in the respective colors.

Moreover, in a case where the determination unit 82 determines the correction by the correction unit 81 to be a "failure", the cause of the failure is specified. For example, in a case where any among the respective representative values of the B1 image, the G image, and the R image exceeds the upper limit threshold value Th2, and the correction thereof is determined to be a failure, the preliminarily captured image 92 being excessively bright is specified as the cause of the correction failure. Additionally, in a case where any among the respective representative values of the B1 image, the G image, and the R image falls below the lower limit threshold value Th1, and the correction thereof is determined to be a failure, the preliminarily captured image 92 being excessively dark is specified as the cause of the correction failure.

Figure 10:
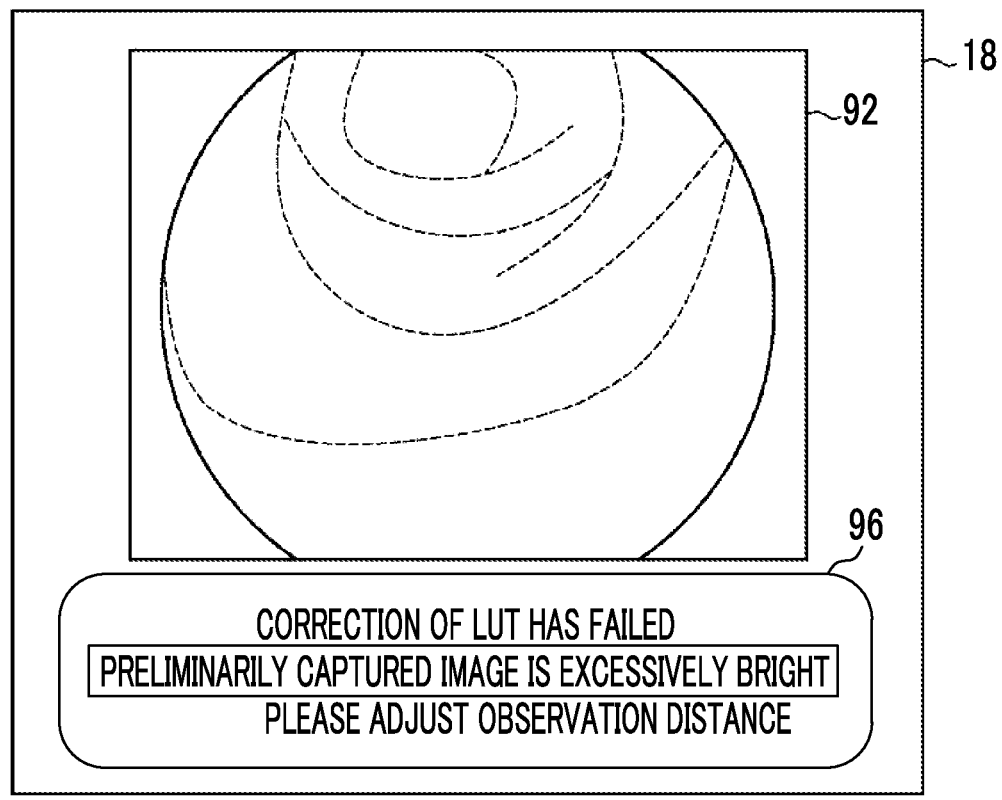
FIG. 10 is a display screen of a monitor displaying a warning.

In a case where a determination result obtained by the determination unit 82 is a failure, the warning unit 83 performs warning by displaying the cause of the failure. For example, in a case where the determination of the determination unit 82 is a "failure" and the specified cause is "the preliminarily captured image 92 being excessively bright", the warning unit 83 displays a warning message 96 on the monitor 18 as illustrated in FIG. 10. The warning message 96 displays, for example, the cause ("a preliminarily captured image being excessively bright") of the failure of the correction of the LUT 75. It is preferable that the warning message 96 displays that the correction of the LUT 75 has failed ("the correction of the LUT failed"), the reason of the failure of the correction of the LUT 75, and a countermeasure method ("Please adjust the observation distance"). In the present embodiment, the warning message 96 is displayed on the monitor 18. However, in a case where the correction of the LUT 75 has failed, any warning methods are adopted as long as the cause of the failure can be notified of. For example, the warning unit 83 can perform warning by means of ON/OFF of a lamp or the like, the vibration pattern of a vibrating member in a case where there is the vibration member, emission of warning sound, or reproduction of a voice message, in addition to the display of the above warning message 96.

Figure 11:
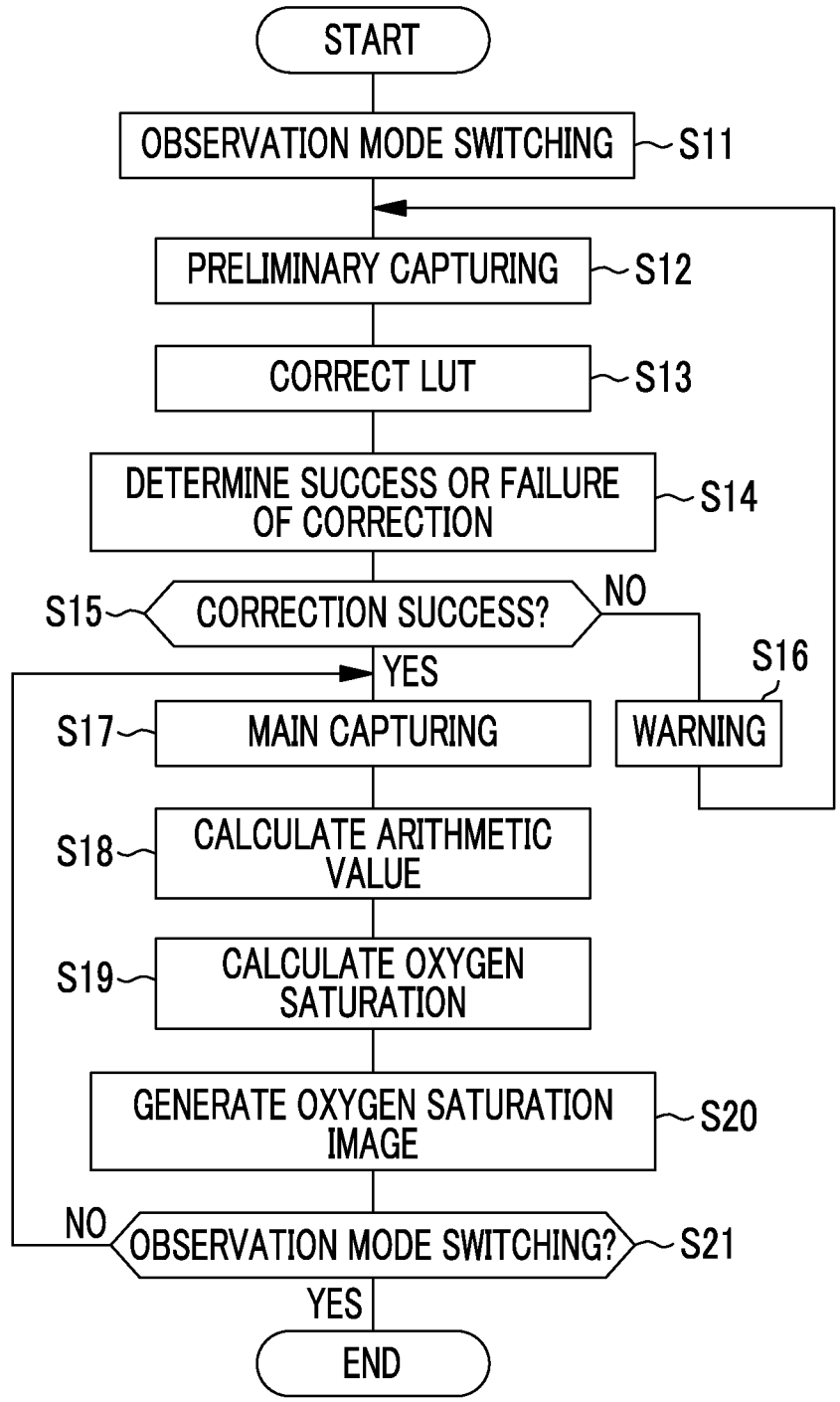
FIG. 11 is a flowchart illustrating a flow of operation in an oxygen saturation mode.

Next, a flow of operation of the endoscope system 10 in a case where the observation object is observed by the oxygen saturation image will be described along a flowchart illustrated in FIG. 11. First, the observation mode is switched to the oxygen saturation observation mode, using the mode changeover switch 13a (S11), the distal end part 12d of an endoscope 12 is directed toward the normal portion of the observation object by the operation of the angle knob 12e or the like, and the preliminary capturing is performed (S12). In a case where the preliminarily captured image 92 is obtained, the correction unit 81 corrects the LUT 75, using the preliminarily captured image 92 (S13). Meanwhile, the determination unit 82 determines a success or failure of the correction of the LUT 75 performed by the correction unit 81, using the preliminarily captured image 92 (S14). As a result of the determination, in a case where the correction is a failure, the warning unit 83 displays the warning message 96 (refer to FIG. 8) showing the cause of the failure of the correction on the monitor 18 (S16). Then, the preliminary capturing is performed again in accordance the warning message 96. The preliminary capturing and the correction of the LUT 75 are repeatedly performed until the determination unit 82 determines the correction by the correction unit 81 to be a success.

In a case where the determination unit 82 determines the correction by the correction unit 81 to be a success (S14), the control unit 52 controls the respective units to perform the main capturing (S17). The image acquisition unit 54 acquires the mainly captured image 91, the arithmetic value calculation unit 71 calculates the ratio B1/G and the ratio R/G, using the mainly captured image 91 (S18), and the oxygen saturation calculation unit 73 calculates the oxygen saturation of the observation object, using the ratio B1/G, the ratio R/G, and the LUT 76 after correction (S19). Then, the oxygen saturation image generation unit 74 generates the base image, using the mainly captured image 91, and applies colors to the generated base image, using the oxygen saturation, to generate the oxygen saturation image (S20). The oxygen saturation image is converted into the format suitable for display by the display control unit 66, and is displayed on the monitor 18. The generation and the display of the oxygen saturation image are repeatedly performed until the observation mode is switched to the normal observation mode, using the mode changeover switch 13a (S21).

As described above, in a case where the observation mode is switched to the oxygen saturation observation mode and the preliminary capturing is performed, the endoscope system 10 not only corrects the original LUT 75, using the preliminarily captured image 92, but also determines a success or failure of the correction of the LUT 75, and performs warning and prompts the preliminary capturing again In a case where the correction of the LUT 75 is a failure. For this reason, the correction of the LUT 75 can be reliably performed in the endoscope system 10.

Additionally, since the warning unit 83 displays the cause of the failure of the correction of the LUT 75, the cause of the failure of the correction of the LUT 75 is clarified by the warning message 96 when the preliminary capturing is performed again. For this reason, the preliminary capturing can be performed again by making an appropriate adjustment such that the correction of the LUT 75 is successful. That is, in a case where the correction of the LUT 75 has failed, the endoscope system 10 displays the cause of the failure by the warning message 96. Thus, the possibility that the correction of the LUT 75 fails continuously due to the same cause can be reduced, and the success rate of the second correction of the LUT 75 can be improved.

In addition, in the above first embodiment, in a case where the observation mode is switched to the oxygen saturation observation mode, the LUT 75 is corrected (S13), and it is determined whether or not the correction of the LUT 75 is a success or failure (S14). However, these turns may be replaced with each other, and whether or not the correction of the LUT 75 is a success or failure may be determined before the LUT 75 is actually corrected. The correction of the LUT 75 and the determination of a success or failure of the correction of the LUT 75 may be performed in parallel.

Additionally, in the above first embodiment, the determination unit 82 compares the calculated representative values calculated, respectively, regarding the B1 image, the G image, and the R image included in the preliminarily captured image 92 with the threshold values (the lower limit threshold value Th1 and the upper limit threshold value Th2), and determines a success or failure of the correction of the LUT 75 by the correction unit 81. However, a success or failure of the correction of the LUT 75 can be determined in accordance with the distribution of the pixel values of the preliminarily captured image 92. The distribution of the pixel values of the preliminarily captured image 92 is, for example, an appearance frequency histogram of the pixel values, and is equal to the distribution of the brightness of the observation object that is reflected on the preliminarily captured image 92 in the case of a monochrome image, such as the B1 image.

Figure 12:
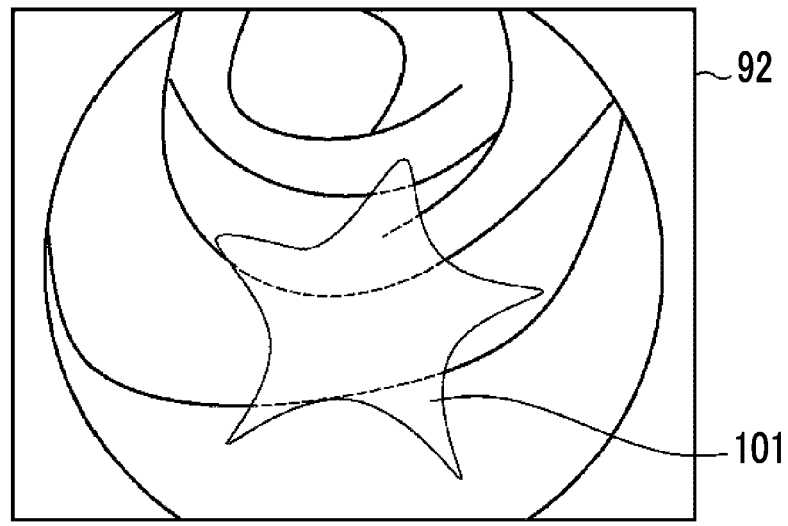
FIG. 12 is a preliminarily captured image with halation.
Figure 13:
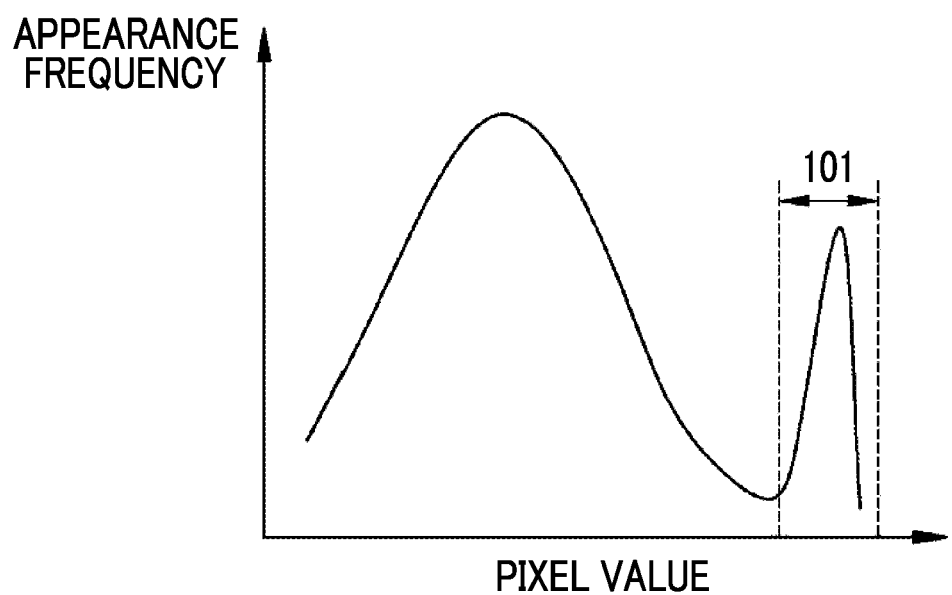
FIG. 13 is an appearance frequency histogram of pixel values.

More specifically, even in a case where it is intended to appropriately capture the normal portion of the observation object, as illustrated in FIG. 12, halation 101 may be generated in the preliminarily captured image 92 at the moment of imaging. In the portion of the halation 101, the values of the ratio B1/G and the ratio R/G become values different from those in a case where the normal portion of the observation object is captured. Thus, in a case where the halation 101 is in the preliminarily captured image 92, the correction of the LUT 75 cannot be accurately performed, either. Even in a case where the halation 101 is in the preliminarily captured image 92 in this way, the correction of the LUT 75 can be determined to be a failure in a case where the representative value of the preliminarily captured image 92 is calculated as in the above embodiment and the calculated representative value is determined as compared to the threshold value. However, the pixels of the portion of the halation 101 have excessively bright pixel values that are clearly far from those in a case where the observation object is normally imaged. For this reason, there is no need to calculate the representative value in many cases, and in a case where the shape (refer to FIG. 13) of the appearance frequency histogram of the pixel values is viewed, it is possible to know the presence or absence of the halation 101. For this reason, the determination unit 82 can determine a success or failure of the correction of the LUT 75 by the appearance frequency histogram of the pixel values of the preliminarily captured image 92. In a case where the cause of a correction failure of the LUT 75 is the halation 101, the warning unit 83 warns of the fact that the halation 101 is in the preliminarily captured image 92 with the warning message 96 or the like.

Additionally, the determination unit 82 can detect an excessively bright portion or an excessively dark portion from the preliminarily captured image 92, determine the correction of the LUT 75 to be a failure in a case where there is an excessively bright portion or an excessively dark portion, and also determine the correction of the LUT 75 to be a success in a case where there is no excessively bright portion or excessively dark portion. That is, the determination unit 82 can also determine the correction of the LUT 75 to be a success or failure by trying to detect the halation 101 or a portion (a portion with small pixel values) where the illumination light does not arrive and is collapsed, from the preliminarily captured image 92. In this case, the determination unit 82 functions as a halation detecting unit or a black collapse detecting unit.

In the above first embodiment, the LUT 75 is corrected because the data that the oxygen saturation calculation unit 73 uses for the calculation of the oxygen saturation is the LUT 75. However, in a case where the oxygen saturation calculation unit 73 calculates the oxygen saturation using data other than the LUT 75, the data is corrected similarly to the above first embodiment. For example, in a case where the oxygen saturation is calculated by a predetermined calculation formula instead of the LUT 75, the type of this calculation formula or the values of coefficients included in the calculation formula correspond to the data used for the calculation of the oxygen saturation. Hence, the oxygen saturation calculation unit 73 includes correction of the calculation formula, the coefficients, or the like in the correction of the data used for the calculation of the oxygen saturation.

Second Embodiment

In the first embodiment, the determination unit 82 determines a success or failure of the correction of the LUT 75 with the pixel values (brightness) of the preliminarily captured image 92. However, a success or failure of the correction of the LUT 75 may be determined with information other than the brightness of the preliminarily captured image 92 instead. For example, the determination unit 82 can detect adhering substances adhering to the observation object using the preliminarily captured image 92, determine the correction of the LUT 75 to be a failure in a case where there are adhering substances, and determine the correction of the LUT 75 to be a success in a case where there are no adhering substances. In this case, the determination unit 82 functions as an adhering substance detecting unit that detects adhering substances on the observation object. The adhering substances of the present embodiment are, for example, adhering substances including a yellow coloring agent (bilirubin or the like), such as residual substances or residual liquid.

Figure 14:
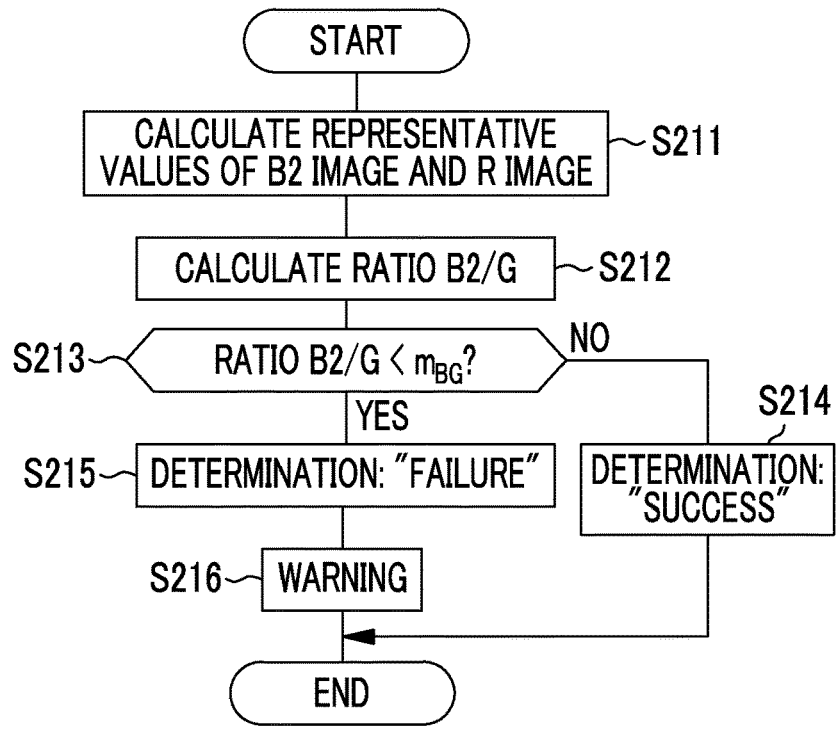
FIG. 14 is a flowchart of a second embodiment in which a success or failure of the correction of the LUT is determined by detecting adhering substances.

In a case where the determination unit 82 detects adhering substances to determine a success or failure of the correction of the LUT 75, as illustrated in FIG. 14, the determination unit 82 calculates the representative values of the B2 image and the G image included in the preliminarily captured image 92 (S211), and calculates the ratio B2/G of these representative values (S212). Since the value of the ratio B2/G becomes smaller as the amount of the residual substances, the residual liquid, or the like becomes larger, the determination unit 82 sets a minimum value $m_{BG}$ that is allowable with respect to the ratio B2/G, and compares the calculated B2/G with the minimum value $m_{BG}$ (S213). Then, the correction of the LUT 75 is determined to be a success in a case where the ratio B2/G is equal to or greater than the minimum value $m_{BG}$ (S214), and the correction of the LUT 75 is determined to be a failure in a case where the ratio B2/G is smaller than the minimum value $m_{BG}$ and the residual substances, the residual liquid, or the like of an amount that is not allowable for the correction of the LUT 75 is detected (S215). In this case, the warning unit 83 warns of the fact that the adhering substances have been detected, by the warning message 96, and prompts cleaning of the observation object before redoing of the preliminary capturing (S216).

In this way, in a case where the adhering substances, such as residual substances or residual liquid, are detected and a success or failure of the correction of the LUT 75 is determined, even in a case where the preliminarily captured image 92 obtained by appropriately imaging the normal portion of the observation object is viewed apparently, the redoing of the preliminary capturing can be prompted in a case where the adhering substances, such as residual substances or residual liquid, are present on the observation object reflected on the preliminarily captured image 92 and the presence of the residual substances is unsuitable for the correction of the LUT 75. Additionally, since the warning unit 83 warns of the fact that the cause of the correction failure of the LUT 75 is the adhering substances, such as residual substances or residual liquid, redoing of the preliminary capturing of the same portion can be prevented by performing only adjustment irrelevant to the cause of a correction failure of the LUT 75, such as changing only an imaging condition (observation distance or the like). Accordingly, a situation where the correction of the LUT 75 fails again can be prevented.

Additionally, in the above second embodiment, the determination unit 82 detects the adhering substances, such as residual substances or residual liquid. However, a success or failure of the correction of the LUT 75 can be determined depending on information on the properties of the observation object (living body functional information or the like).

Figure 15:
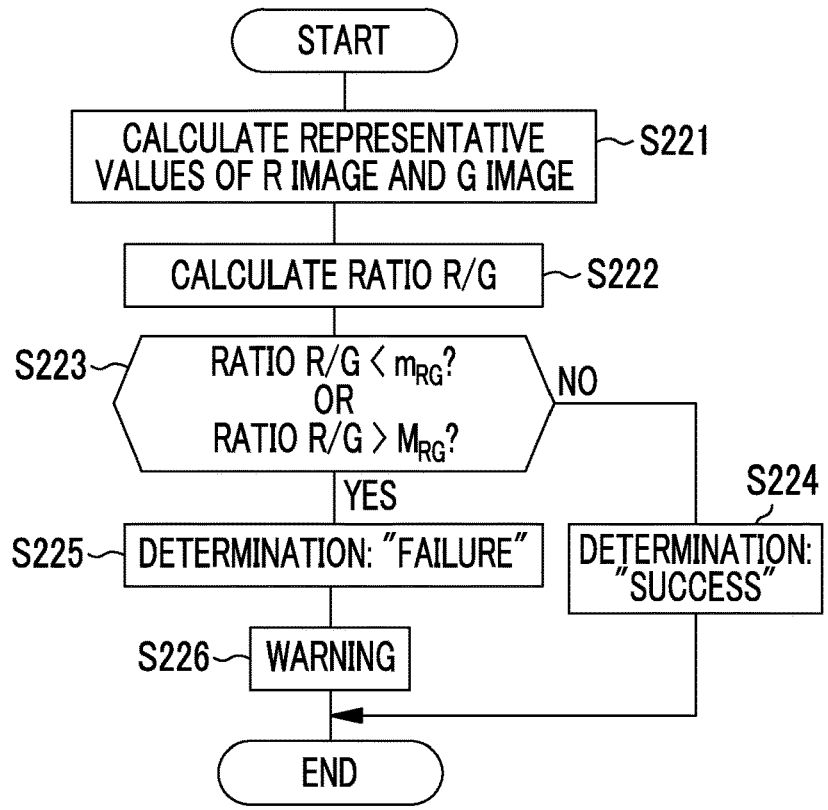
FIG. 15 is a flowchart in a case where a success or failure of the correction of the LUT is determined depending on the amount of blood.

For example, the range of the amount of blood of the observation object can be set, and in a case where the amount of blood does not fall within the set range, the correction of the LUT 75 can be determined to be a failure. In this case, as illustrated in FIG. 15, the determination unit 82 calculates the representative values of the R image and the G image in the preliminarily captured image 92 (S221), and calculates the ratio R/G of these representative values (S222). The determination unit 82 sets a maximum value $M_{RG}$ and a minimum value $m_{RG}$ that are allowed for the ratio R/G, and compares the calculated ratio R/G with the maximum value $M_{RG}$ and the minimum value $m_{RG}$ (S223). In a case where the ratio R/G is equal to or smaller than the maximum value $M_{RG}$ and the ratio R/G is equal to or greater than the minimum value $m_{RG}$, the determination unit 82 determines the correction of the LUT 75 to be a success (S224). On the other hand, in a case where the ratio R/G exceeds the maximum value $M_{RG}$ or in a case where the ratio R/G falls below the minimum value $m_{RG}$, the determination unit 82 determines the correction of the LUT 75 to be a failure (S225). Then, the warning unit 83 warns of the fact that the amount of blood is excessive (the case of Ratio R/G>Maximum value $M_{RG}$) or that the amount of blood is insufficient (Ratio R/G<Minimum value $m_{RG}$), with the warning message 96, and prompts the portion to be imaged in the preliminary capturing to be changed (S226). Accordingly, for example, even in a case where a portion, which looks normal apparently but is unsuitable for the correction of the LUT 75, such as a portion where extremely slight redness, atrophy, or the like, is present broadly, is preliminarily captured, redoing of the preliminary capturing can be prompted. Particularly, the warning unit 83 warns of the fact that the amount of blood is in an unsuitable range. Thus, in the redoing of the preliminary capturing, the preliminary capturing of the same portion can be prevented by performing only adjustment irrelevant to the cause of a correction failure of the LUT 75, such as changing only an imaging condition (observation distance or the like). Accordingly, a situation where the correction of the LUT 75 fails again can be prevented.

It is particularly preferable to combine the determination based on the allowable range of the above amount of blood with the determination performed by detecting the adhering substances. This is because the value of the ratio B2/G varies depending on the residual substances, the residual liquid, or the like, but also varies depending on the amount of blood. Specifically, the determination unit 82 determines the correction of the LUT 75 to be a failure in any of a case where the ratio B2/G is smaller than the minimum value $m_{BG}$, a case where the ratio R/G exceeds the maximum value $M_{RG}$, and a case where the ratio R/G falls below the minimum value $m_{RG}$. Then, the warning unit 83 warns of any one or a plurality of ones of the facts that the adhering substances have been detected (the case of Ratio B2/G<Minimum value $m_{BG}$), the amount of blood is excessive (the case of Ratio R/G>Maximum value $M_{RG}$), and the amount of blood is insufficient (Ratio R/G<Minimum value $m_{RG}$), with the warning message 96.

In addition, it is preferable to change the minimum value $m_{BG}$ of the ratio B2/G depending on the value of the ratio R/G. This is because the value of the ratio B2/G also varies depending on the amount of blood. In a case where the minimum value $m_{BG}$ to the ratio B2/G is changed depending on the value of the ratio R/G, the presence or absence of the adhering substances can be detected more accurately.

In the modification example of the above second embodiment, a success or failure of the correction is determined depending on the amount of blood. However, a success or failure of the correction can be determined using information on the properties of the observation object represented by a ratio in the preliminarily captured image 92 other than the amount of blood.

In the above second embodiment and the above modification example, a so-called "ratio of the preliminarily captured image 92" is obtained by calculating the representative values of the preliminarily captured image 92 in the respective colors and calculating the ratio of the calculated representative values. However, the ratio of the preliminarily captured image 92 may be calculated by other methods. For example, an average value of ratios B2/G of respective pixels can be obtained after the ratio B2/G is calculated for each pixel. In any case, in the above second embodiment and the above modification example, the determination unit 82 determines a success or failure of the correction, using the ratio of the preliminarily captured image 92.

In the above second embodiment and the above modification example, the B2 image in the preliminarily captured image 92 is used. However, the B1 image may be used instead of the B2 image.

Third Embodiment

Figure 16:
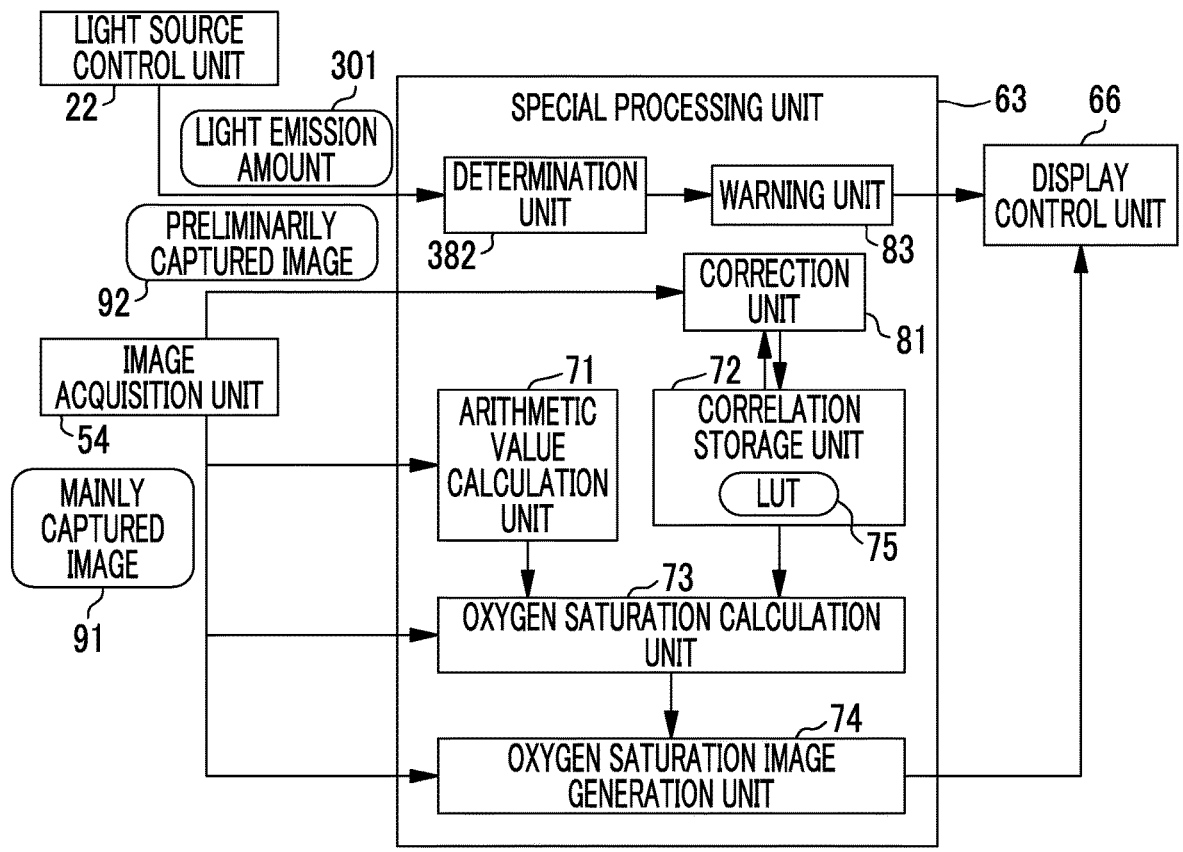
FIG. 16 is a block diagram of a special processing unit of a third embodiment.

In the first and second embodiments, the determination unit 82 can determine a success or failure of the correction of the LUT 75, using the preliminarily captured image 92. However, the determination unit 82 may determine a success or failure of the correction of the LUT 75, using information other than the preliminarily captured image 92. For example, as illustrated in FIG. 16, a determination unit 382 acquires the light emission amounts 301 of the respective light sources 20a to 20d in a case where the preliminary capturing is performed, from the light source control unit 22, and determines a success or failure of the correction of the LUT 75 depending on the light emission amounts 301 of the respective light sources 20a to 20d.

The light source control unit 22 adjusts the light emission amounts 301 of the respective light sources 20a to 20d, such as increasing the light emission amounts 301 in a case where the observation distance becomes long so that the observation object can be continuously imaged with as constant brightness as possible irrespective of the observation distance. For this reason, the light emission amounts 301 of the respective light sources 20a to 20d substantially depends on the observation distance, the light emission amounts 301 are large in a case where the observation distance is long, and the light emission amounts 301 are small in a case where the observation distance is short. For this reason, the determination unit 382 calculates an observation distance $D_a$, using the light emission amounts 301, and compares the observation distance $D_a$ with the shortest observation distance $D_m$ that is set in advance and is allowable in the preliminary capturing.

In a case where the calculated observation distance $D_a$ is shorter than the shortest observation distance $D_m$ (specific distance) ($D_a<D_m$), the determination unit 82 determine the correction of the LUT 75 to be a failure. This is because, in a case where the observation distance is shorter than the shortest observation distance $D_m$, the distal end of the endoscope 12 excessively approaches the observation object, and thus, the radiation unevenness of the illumination light occurs. In this case, the warning unit 83 warns of the fact that the observation distance is excessively short, with the warning message 96, and prompts adjustment of the observation distance to perform the preliminary capturing.

In the above third embodiment, only the shortest observation distance $D_m$ is set. However, the longest observation distance $D_M$ may also be set, and even in a case where the calculated observation distance $D_a$ is longer than the longest observation distance $D_M$ ($D_a>D_M$), the correction of the LUT 75 may be determined to be a failure. This is because, in a case where the calculated observation distance $D_a$ is longer than the longest observation distance $D_M$, the respective light sources 20a to 20d reach their maximum light quantities and the preliminarily captured image 92 tends to become dark.

In the above third embodiment, the observation distance is calculated depending on the light emission amounts 301. However, the observation distance can also be calculated using information other than the light emission amounts 301 (for example, the preliminarily captured image 92).

Fourth Embodiment

Since the observation object is a mucous membrane or the like of a living body and the endoscope 12 is flexible and freely movable, there is relative movement (hereinafter simply referred to as movement) between the observation object and the endoscope 12. In the preliminary capturing, the observation object is sequentially imaged with the B1 light, the B2 light, the G light, and the R light. However, in a case where there is the movement between these kinds of imaging, there is a case where the correction of the LUT 75 may become inaccurate. In consideration of this, the determination unit 82 can detect the movement, using the preliminarily captured image 92, and determine a success or failure of the correction of the LUT 75 depending on the magnitude of the detected movement. In this case, the determination unit 82 functions as a movement detecting unit.

Figure 17:
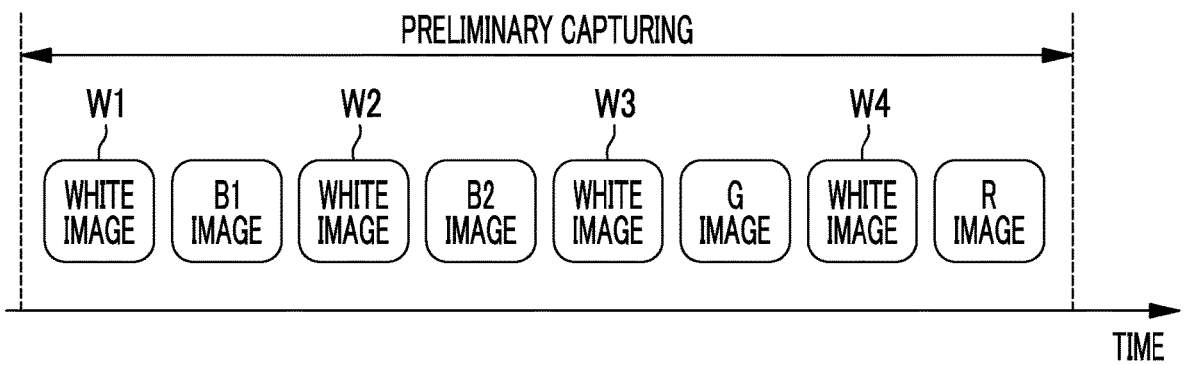
FIG. 17 is an explanatory view illustrating an image acquired by preliminary capturing that detects movement.

In a case where the determination unit 82 detects the movement as described above, the light source control unit 22 performs sequential switchings to, for example, the white light, the B1 light, the white light, the B2 light, the white light, the G light, the white light, and the R light in the case of the preliminary capturing. That is, the white light is sandwiched between the sequential switchings to the B1 light, the B2 light, the G light, and the R light. Accordingly, as illustrated in FIG. 17, the image acquisition unit 54 sequentially acquires a white image W1, the B1 image, a white image W2, the B2 image, a white image W3, the G image, a white image W4, and the R image obtained by imaging the observation object at respectively different times. Hence, in a case where the determination unit 82 detects the movement, these eight images are included in the preliminarily captured image 92.

The correction unit 81 corrects the LUT 75, using a required image among the B1 image, the B2 image, the G image, and the R image in the preliminarily captured image 92. The method of correcting the LUT 75 is the same as that of the first embodiment and the like.

The determination unit 82 detects the movement, using the four white images W1 to W4 in the preliminarily captured image 92. Specifically, for example, representative values of red components (hereinafter referred to as an R component) of these four white images W1 to W4 are calculated, respectively, a standard deviation and an average value of the calculated four representative values are calculated, and the ratio of the standard deviation and the average value (standard deviation/average value) is set as the magnitude of the movement. Then, the determination unit 82 compares the magnitude Md of the detected movement with a preset upper limit value $T_M$. In a case where the magnitude Md of the detected movement is greater than the upper limit value $T_M$ (Md>$T_M$), the determination unit 82 determines the correction of the LUT 75 to be a failure, and the warning unit 83 warns of the fact that the correction of the LUT 75 has failed due to a great movement, with the warning message 96.

As described above, in a case where the movement is detected and a success or failure of the correction is determined depending on the magnitude of the LUT 75, a success or failure of the correction of the LUT 75 can be accurately determined even in a case where the LUT 75 can be accurately corrected due to the presence of the movement.

In addition, in a case where the movement is detected and a success or failure of the correction of the LUT 75 is determined depending on the magnitude of the movement, the determination unit 82 captures the white images W1 to W4 between the B1 image, the B2 image, the G image, and the R image. This is performed in order to accurately detect the movement. Although the movement can also be detected using the B1 image, the B2 image, the G image, and the R image, these are different from each other in illumination light. Thus, there is a difference between subjects reflected on the images in the respective colors. For example, although so-called surface layer blood vessels in the vicinity of the surface of a mucous membrane are well reflected on the B1 image or the B2 image, these vessels are seldom viewed in the R image. For this reason, in a case where images, such as B1 images or R images, obtained by imaging the observation object with monochrome illumination light are combined with each other and used for the detection of the movement, there is a case where the detection accuracy of the movement may not be not good, and consequently, the accuracy of determination of a success or failure of the correction of the LUT 75 may also be not good. In contrast, in a case where the white images W1 to W4 are used for the detection of the movement, these images have the same conditions of illumination light. Thus, the movement can be detected accurately.

In the above fourth embodiment, the movement is detected using the white images W1 to W4. However, the movement can also be accurately detected using G images other than these images W1 to W4. In a case where the images with the same conditions of illumination light are used for the detection of the movement, the detection accuracy of the movement improves compared to a case where images obtained by imaging the observation object with monochrome illumination light are combined with each other. For this reason, the movement can also be detected by acquiring two or more of any of the B1 images, the B2 images, the G images, or the R images that the correction unit 81 uses for the correction of the LUT 75, in the preliminary capturing, and by using the same color of two or more acquired images. That is, it is preferable that the determination unit 82 detects the movement, using a plurality of the preliminarily captured images 92 obtained by imaging the observation object with the same illumination light, among the plurality of preliminarily captured images 92.

Fifth Embodiment

In a case where a treatment tool (hereinafter referred to as an artificial object), such as the insertion part 12a of the endoscope 12 and forceps, is reflected on the preliminarily captured image 92, the treatment tool is not present in the normal portion of the observation object. Thus, there is a case where the correction unit 81 may not correct the LUT 75 accurately. For this reason, it is preferable that the determination unit 82 detects the reflection of the artificial object on the preliminarily captured image 92, and a success or failure of the correction of the LUT 75 is determined due to the presence or absence of the reflection of the artificial object. In this case, the determination unit 82 functions as an artificial object detecting unit that detects the artificial object, determines the correction of the LUT 75 to be a failure in a case where the reflection of the artificial object is detected on the preliminarily captured image 92, and determines the correction of the LUT 75 to be a success in a case where there is no reflection of the artificial object on the preliminarily captured image 92. In a case where the correction of the LUT 75 is determined to be a failure because the determination unit 82 has detected the reflection of the artificial object, the warning unit 83 warns of the event, with the warning message 96, and prompts the preliminary capturing in a state where there is no reflection of the artificial object.

The reflection of the artificial object can be detected, for example, depending on the ratio of the preliminarily captured image 92 as in the second embodiment and the modification example of the second embodiment. For example, in a case where the ratio of the preliminarily captured image 92 indicates an abnormal value that is not within a range capable of being taken in a case where there is the normal portion of the observation object or the adhering substances, discrimination from the reflection of the artificial object can be made.

Sixth Embodiment

Figure 18:
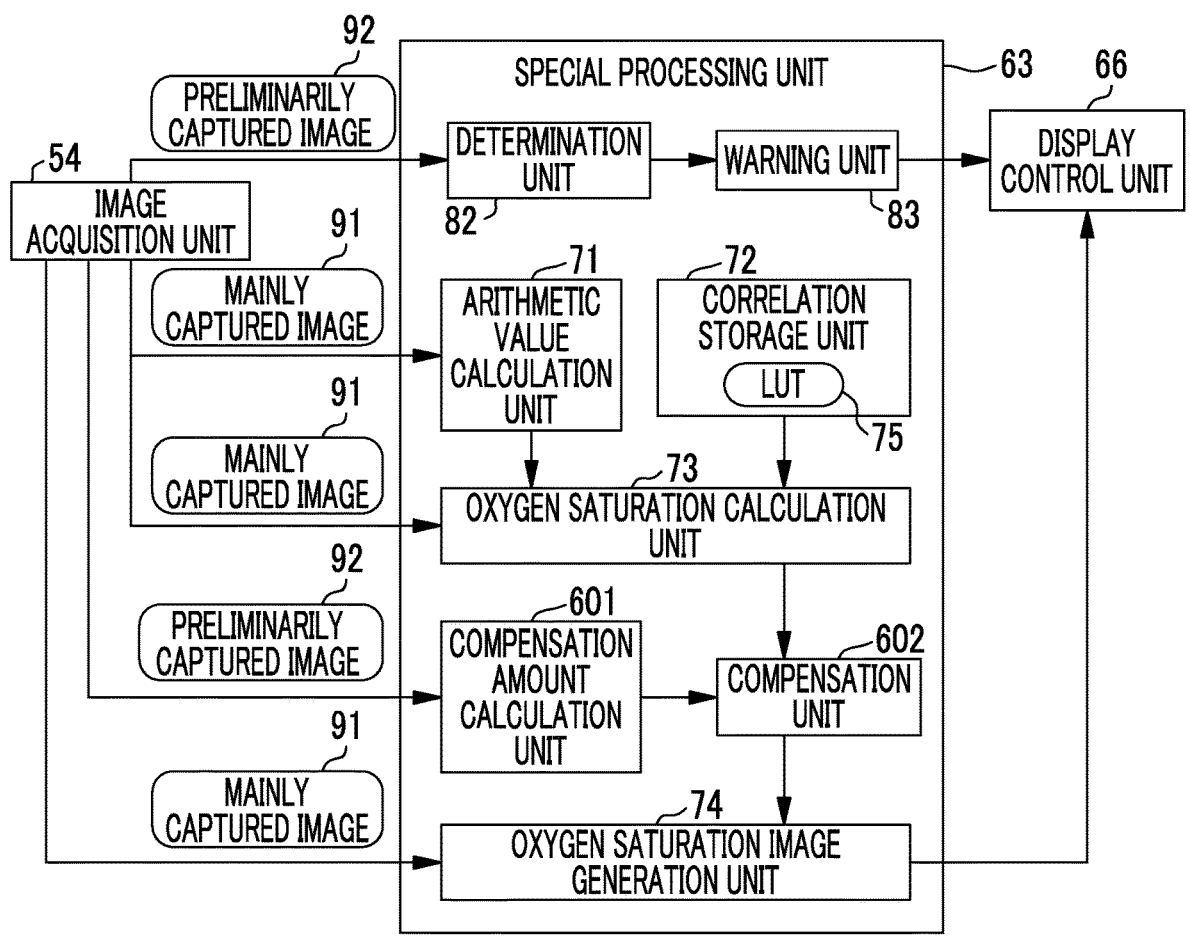
FIG. 18 is a block diagram of a special processing unit of a sixth embodiment.

In the above first to fifth embodiments, the special processing unit 63 has the correction unit 81 that corrects the LUT 75. However, the value of the oxygen saturation calculated by the oxygen saturation calculation unit 73 may be compensated for instead of the correction of the LUT 75. In this case, as illustrated in FIG. 18, the special processing unit 63 is provided with a compensation amount calculation unit 601 and a compensation unit 602 instead of the correction unit 81.

Similar to the first embodiment, the oxygen saturation calculation unit 73 refers to the LUT 75, and calculates the oxygen saturation corresponding to the ratio B1/G and the ratio R/G calculated by the arithmetic value calculation unit 71. However, in the present embodiment, the preliminary capturing is performed, but the LUT 75 is not corrected. For this reason, the LUT 75 that the oxygen saturation calculation unit 73 uses for the calculation of the oxygen saturation is always the LUT 75 that the correlation storage unit 72 stores from the beginning.

Instead of this, the compensation amount calculation unit 601 and the compensation unit 602 acquire the preliminarily captured image 92 from the image acquisition unit 54, and compensates for the value of the oxygen saturation calculated by the oxygen saturation calculation unit 73 calculates, using the preliminarily captured image 92. Specifically, the compensation amount calculation unit 601 calculates the ratio B1/G and the ratio R/G, using the B1 image, the G image, and the R image of the preliminarily captured image 92, and calculates representative values of the calculated ratio B1/G and the ratio R/G for each pixel. Then, the oxygen saturation corresponding to the representative values of the ratio B1/G and the ratio R/G is obtained referring to the LUT 75.

Figure 19:
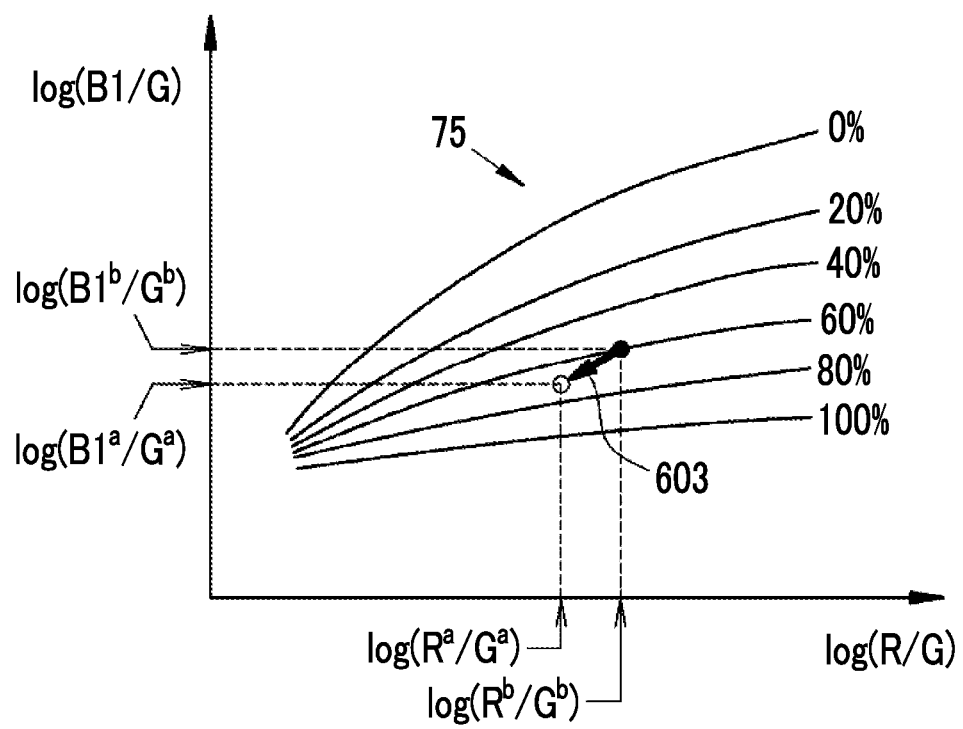
FIG. 19 is a graph illustrating a method of calculating the amount of compensation.

For example, as illustrated in FIG. 19, the representative value of the ratio B1/G calculated using an image obtained by imaging the normal portion of the ideal observation object becomes $B1^a/G^a$, the representative value of the ratio R/G becomes $R^a/G^a$, the representative value of the ratio B1/G calculated using the preliminarily captured image 92 is $B1^b/G^b$, and the representative value of the ratio R/G calculated using the preliminarily captured image 92 is $R^b/G^b$. In FIG. 19, for example, the oxygen saturation corresponding to the $B1^a/G^a$ and $R^a/G^a$ is 70%, and the oxygen saturation corresponding to $B1^b/G^b$ and $R^b/G^b$ is 60%.

The compensation amount calculation unit 601 calculates a compensation amount 603 for the oxygen saturation calculated by the oxygen saturation calculation unit 73, from a relationship between an oxygen saturation (70%) used as reference in a case where an image obtained by imaging the normal portion of the ideal observation object is used, and an oxygen saturation (60%) calculated using the actual preliminarily captured image 92. In the case of the above FIG. 19, the compensation amount 603 is "+10%".

The compensation unit 602 compensates for the oxygen saturation calculated by the oxygen saturation calculation unit 73 in accordance with the compensation amount 603 calculated by the compensation amount calculation unit 601. For example, the compensation amount 603 is "+10%", and in a case where the oxygen saturation of a pixel calculated by the oxygen saturation calculation unit 73 is "50%", the compensation unit 602 compensates for the oxygen saturation of the pixel to "60%(=50%+10%)".

The oxygen saturation image generation unit 74 generates a base image, using the mainly captured image 91, and applies colors to the generated base image, using the oxygen saturation, to generate the oxygen saturation image. However, in the present embodiment, the oxygen saturation image generation unit 74 does not use the oxygen saturation calculated by the oxygen saturation calculation unit 73 as it is, but uses the oxygen saturation compensated for by the compensation unit 602.

Additionally, in the present embodiment, the compensation amount calculation unit 601 and the compensation unit 602 are provided instead of the correction unit 81. Thus, the determination unit 82 acquires the preliminarily captured image 92 that the compensation amount calculation unit 601 uses from the image acquisition unit 54, and determines a success or failure of the compensation performed by the compensation unit 602. A method for the determination and a method of specifying a cause in a case where the compensation is determined to be a failure are the same as those of the first embodiment and the like. In a case where the determination unit 82 determines the compensation performed by the compensation unit 602 to be a failure, the way in that the warning unit 83 displays the cause of the compensation failure, warns of the fact with the warning message 96 or the like, and prompts redoing of the preliminary capturing is also the same as that of the first embodiment and the like.

Figure 20:
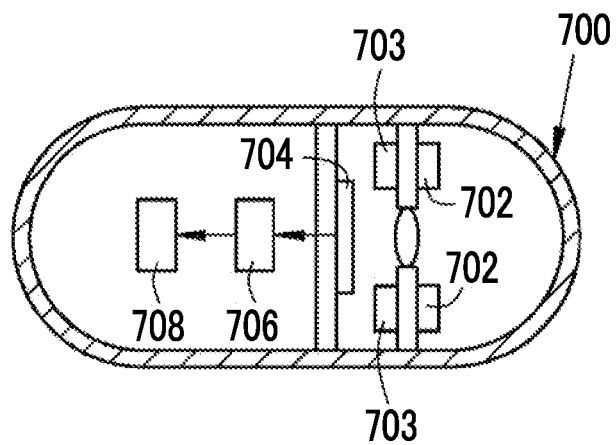
FIG. 20 is a schematic view of a capsule endoscope.

In addition, in the above first to sixth embodiments, the invention is carried out by the endoscope system that performs observation by inserting the endoscope 12 provided with the image sensor 48 into a subject. However, a capsule endoscope system is also suitable for the invention. For example, as illustrated in FIG. 20, the capsule endoscope system has at least a capsule endoscope 700 and a processor device (not illustrated).

A capsule endoscope 700 includes a light source 702, a control unit 703, an image sensor 704, an image processing unit 706, and a transmission/reception antenna 708. The light source 702 corresponds to the light source unit 20. The control unit 703 functions similarly to the light source control unit 22 and the control unit 52. Additionally, the control unit 703 is capable of wirelessly communicating with a processor device of a capsule endoscope system by the transmission/reception antenna 708. Although the processor device of the capsule endoscope system is substantially the same as that of the above processor device 16 of the first to sixth embodiment, the image processing unit 706 corresponding to the image acquisition unit 54 and the image processing unit 61 is provided in the capsule endoscope 700, and the generated oxygen saturation image 77 or the like is transmitted to the processor device via the transmission/reception antenna 708. The image sensor 704 is configured similarly to the image sensor 48.

EXPLANATION OF REFERENCES

10: endoscope system
16: processor device
54: image acquisition unit
61: image processing unit
62: normal processing unit
63: special processing unit
71: arithmetic value calculation unit
73: oxygen saturation calculation unit
74: oxygen saturation image generation unit
75: look-up table (LUT)
81: correction unit
82, 382: determination unit
83: warning unit
91: mainly captured image
92: preliminarily captured image
96: warning message
301: light emission amount
601: compensation amount calculation unit
602: compensation unit
700: capsule endoscope

What is claimed is:

1. An endoscope system comprising: a processor configured to: calculate oxygen saturation of an observation object as a data; acquire at least one image of the observation object; correct the data using the at least one image; determine a success or a failure of the correction as a determination result; and perform warning in a case where the determination result is the failure, wherein the data is corrected by calculating a correction amount, the correction amount is obtained by a relationship between oxygen saturation used as reference and oxygen saturation calculated using a preliminarily captured image, and one of configurations i) to vii) below is set:
  i) the acquired at least one image being a plurality of images obtained by imaging the observation object with a plurality of illumination light beams having different wavelength ranges, respectively, and determining the success or the failure of the correction comprising: determining the success or the failure of the correction for each of the images;
  ii) the acquired at least one image being an image, and determining the success or the failure of the correction comprising: determining the success or the failure of the correction depending on a brightness of the image;
  iii) the acquired at least one image being an image, and determining the success or the failure of the correction comprising: determining the success or the failure of the correction depending on a distribution of pixel values of the image;
  iv) the acquired at least one image being an image, and determining the success or the failure of the correction comprising: detecting an excessively bright portion or an excessively dark portion from the image, determining the correction to be the failure in a case where the excessively bright portion or the excessively dark portion is present, and determining the correction to be the success in a case where there is no excessively bright portion or excessively dark portion;
  v) the acquired at least one image being a plurality of images obtained by imaging the observation object with a plurality of illumination light beams having different wavelength ranges, respectively, and determining the success or the failure of the correction comprising: determining the success or the failure of the correction using a ratio of the plurality of images;
  vi) the acquired at least one image being an image, and determining the success or the failure of the correction comprising: determining the success or the failure of the correction depending on a light emission amount of illumination light when the image is captured;
  vii) the acquired at least one image being an image, and determining the success or the failure of the correction comprising: detecting, using the image, a relative movement between the observation object and an endoscope that images the observation object, and determining the success or the failure of the correction depending on a magnitude of the detected relative movement; and wherein the processor is further configured to perform each of the configurations i) to vii), and the processor is configured to set one of the configurations i) to vii) when determining the determination result.

2. The endoscope system according to claim 1,
wherein the configuration v) is set, and
wherein determining the success or the failure of the correction using the ratio of the plurality of images comprises: detecting an adhering substance adhering to the observation object, determining the correction to be the failure in a case where there is an adhering substance, and determining the correction to be the success in a case where there is no adhering substance.

3. The endoscope system according to claim 1,
wherein the configuration v) is set, and
wherein determining the success or the failure of the correction using the ratio of the plurality of images comprises: determining the success or the failure of the correction depending on information on properties of the observation object represented by the ratio of the plurality of images.

4. The endoscope system according to claim 3,
wherein determining the success or the failure of the correction depending on the information on the properties of the observation object represented by the ratio of the plurality of images comprises: determining the success or the failure of the correction depending on an amount of blood.

5. The endoscope system according to claim 1,
wherein the configuration v) is set, and
wherein determining the success or the failure of the correction using the ratio of the plurality of images comprises: detecting reflection of an artificial object, determining the correction to be the success in a case where there is no reflection of the artificial object, and determining the correction to be the failure in a case where there is the reflection of the artificial object.

6. The endoscope system according to claim 1,
wherein the configuration vi) is set, and
wherein determining the success or the failure of the correction depending on the light emission amount of illumination light when the image is captured comprises: calculating an observation distance using the light emission amount, and determining the success or the failure of the correction depending on the observation distance.

7. The endoscope system according to claim 6,
wherein determining the success or the failure of the correction depending on the observation distance comprises: determining the correction to be the failure in a case where the observation distance is shorter than a specific distance.

8. The endoscope system according to claim 1,
wherein the configuration vii) is set, and
wherein detecting the relative movement between the observation object and the endoscope that images the observation object comprises: detecting the relative movement, using a plurality of images obtained by imaging the observation object with the same illumination light, in the image.

9. The endoscope system according to claim 1,
wherein the processor is configured to display a message on a display unit.

10. A processor device comprising: a processor configured to: calculate an oxygen saturation of an observation object as a data; acquire at least one image of the observation object; correct the data using the at least one image; determine a success or a failure of the correction as a determination result; and perform warning in a case where the determination result is the failure, wherein the data is corrected by calculating a correction amount, the correction amount is obtained by a relationship between oxygen saturation used as reference and oxygen saturation calculated using a preliminarily captured image, and one of configurations i) to vii) below is set: i) the acquired at least one image being a plurality of images obtained by imaging the observation object with a plurality of illumination light beams having different wavelength ranges, respectively, and determining the success or the failure of the correction comprising: determining the success or the failure of the correction for each of the images; ii) the acquired at least one image being an image, and determining the success or the failure of the correction comprising: determining the success or the failure of the correction depending on a brightness of the image; iii) the acquired at least one image being an image, and determining the success or the failure of the correction comprising: determining the success or the failure of the correction depending on a distribution of pixel values of the image; iv) the acquired at least one image being an image, and determining the success or the failure of the correction comprising: detecting an excessively bright portion or an excessively dark portion from the image, determining the correction to be the failure in a case where the excessively bright portion or the excessively dark portion is present, and determining the correction to be the success in a case where there is no excessively bright portion or excessively dark portion; v) the acquired at least one image being a plurality of images obtained by imaging the observation object with a plurality of illumination light beams having different wavelength ranges, respectively, and determining the success or the failure of the correction comprising: determining the success or the failure of the correction using a ratio of the plurality of images; vi) the acquired at least one image being an image, and determining the success or the failure of the correction comprising: determining the success or the failure of the correction depending on a light emission amount of illumination light when the image is captured; vii) the acquired at least one image being an image, and determining the success or the failure of the correction comprising: detecting, using the image, a relative movement between the observation object and an endoscope that images the observation object, and determining the success or the failure of the correction depending on a magnitude of the detected relative movement; and wherein the processor is further configured to perform each of the configurations i) to vii), and the processor is configured to set one of the configurations i) to vii) when determining the determination result.

11. A method of operating an endoscope system having a processor being configured to calculate an oxygen saturation of an observation object as a data, the method comprising: acquiring at least one image of the observation object by the processor; correcting the data using the at least one image by the processor; determining a success or a failure of the correction as a determination result by the processor; and performing warning through the processor in a case where the determination result is the failure, wherein the data is corrected by calculating a correction amount, the compensation correction amount is obtained by a relationship between oxygen saturation used as reference and oxygen saturation calculated using a preliminarily captured image, and one of configurations i) to vii) below is set: i) the acquired at least one image being a plurality of images obtained by imaging the observation object with a plurality of illumination light beams having different wavelength ranges, respectively, and determining the success or the failure of the correction comprising: determining the success or the failure of the correction for each of the images; ii) the acquired at least one image being an image, and determining the success or the failure of the correction comprising: determining the success or the failure of the correction depending on a brightness of the image; iii) the acquired at least one image being an image, and determining the success or the failure of the correction comprising: determining the success or the failure of the correction depending on a distribution of pixel values of the image; iv) the acquired at least one image being an image, and determining the success or the failure of the correction comprising: detecting an excessively bright portion or an excessively dark portion from the image, determining the correction to be the failure in a case where the excessively bright portion or the excessively dark portion is present, and determining the correction to be the success in a case where there is no excessively bright portion or excessively dark portion; v) the acquired at least one image being a plurality of images obtained by imaging the observation object with a plurality of illumination light beams having different wavelength ranges, respectively, and determining the success or the failure of the correction comprising: determining the success or the failure of the correction using a ratio of the plurality of images; vi) the acquired at least one image being an image, and determining the success or the failure of the correction comprising: determining the success or the failure of the correction depending on a light emission amount of illumination light when the image is captured; vii) the acquired at least one image being an image, and determining the success or the failure of the correction comprising: detecting, using the image, a relative movement between the observation object and an endoscope that images the observation object, and determining the success or the failure of the correction depending on a magnitude of the detected relative movement; and wherein the processor is further configured to perform each of the configurations i) to vii), and the processor is configured to set one of the configurations i) to vii) when determining the determination result.

\* \* \* \* \*